United States Patent [19]

Wissler

[11] Patent Number: 4,514,387

[45] Date of Patent: Apr. 30, 1985

[54] CHEMOKINESINS AND CHEMOTAXINS OF LEUKOCYTES AND INFLAMED TISSUES

[75] Inventor: Josef H. Wissler, Bad Nauheim, Fed. Rep. of Germany

[73] Assignee: Max-Planck-Gesellschaft zur Forderung der Wissenschaften, Gottingen, Fed. Rep. of Germany

[21] Appl. No.: 358,097

[22] Filed: Mar. 15, 1982

[30] Foreign Application Priority Data

Mar. 18, 1981 [DE] Fed. Rep. of Germany ....... 3110610

[51] Int. Cl.3 .................. A61K 39/395; A61K 37/02; C07G 7/00; C12P 21/00

[52] U.S. Cl. ................................ 424/85; 260/112 R; 435/68; 514/21

[58] Field of Search ....................... 260/112 R, 112 B; 424/88, 101, 85, 177; 435/68, 240, 241

[56] References Cited

PUBLICATIONS

Gallin, J., et al., "Leukocyte Chemotaxis: Methods, Physiology, and Clinical Implications", Raven Press, New York, 1976, (Table of Contents).

Hayashi, I., Nature, vol. 259, pp. 132–134, 1976.

Ingram, D., "Biological Activities of Complement", Karger, Basel, pp. 132–157, 1972.

Iscove, N., et al., J. Exp. Med., vol 147, pp. 923–933, 1978.

Whiples, H., et al., Ann., N.Y. Acad. Sci., vol. 1B, pp. 511–1092, 1964.

Bloom, B., "In Vitro Methods In Cell-Mediated and Tumor Immunity", Academic Press, N.Y., 1976, Table of Contents.

Buckley, I., Exp. Mol. Pathology, vol. 2, pp. 402–417, 1963.

"Biological Safety Tests", European Pharmacopoeia, vol. II, pp. 56–60, 1971.

Menkin, V., "Biochemical Mechanisms In Inflammation", Charles C. Thomas, Springfield, Ill., 1956 (Table of Contents).

Peterson, S., et al., Biophysical Journal, vol. 12, pp. 1048–1055, 1972.

Rich, A., et al., Bull., Johns Hopkins Hospital, vol. 50, No. 2, pp. 115–131, 1931.

Wilkinson, P., "Chemotaxis and Inflammation", Churchill Livingstone, Edinburgh and London, 1974 (Table of Contents).

Wissler, J., Eur. J. Immunol., vol. II, pp. 73–96, 1972.

Damerau et al., Naunyn-Schmiedeberg's Arch. Pharmacol., vol. 302, pp. 45–50, 1978.

Andersson et al., J. Exp. Med., vol. 137, pp. 943–953, 1973.

Ward et al., Science, vol. 163, pp. 1079–1081, 1969.

Chemical Abstracts, vol. 90, Abst. No. 20609s, 1979.

Chemical Abstracts, vol. 88, Abst. No. 103162a, 1978.

Clausen, The Journal of Immunology, vol. 108, pp. 453–459, 1972.

Merriman, C., et al., Proc. Soc. Exp. Biol., vol. 149, pp. 782–784, 1975.

Ward et al., J. Exp. Med., vol. 127, pp. 693–709, 1968.

Boyden, S., J. Exp. Med. vol. 115, pp. 453–466, 1962.

*Primary Examiner*—Blondel Hazel

*Attorney, Agent, or Firm*—Cooper, Dunham, Clark, Griffin & Moran

[57] ABSTRACT

The invention relates to new chemokinesins and chemotaxins of leukocytes and inflamed tissue which have the biological and physico-chemical properties stated in the patent claims. The compounds selectively influence the motility of leukocytes or selectively attract leukocytes. The invention also relates to a biotechnical process for preparing and isolating the chemokinesins and chemotaxins and to pharmaceutical compositions containing them.

46 Claims, 15 Drawing Figures

FIG. 1 ABSORPTION SPECTRUM OF LYMPHOCYTO-MONOAPOKINESINS IN WATER AT 20°C. EXTINCTION SCALE (0-100) E = 0-2 AT A LIGHT PATH d = 1 cm.

FIG. 2 ABSORPTION SPECTRUM OF MONOCYTO-GRANULOAPOKINESINS IN WATER AT 20°C. EXTINCTION SCALE (0-100) E = 0-2 AT A LIGHT PATH d = 1 cm.

FIG. 3 ABSORPTION SPECTRUM OF MONOCYTO-GRANULOPROSKINESIN IN WATER AT 20°C. EXTINCTION SCALE (0-100 E = 0-2 AT A LIGHT PATH d = 1 cm.

FIG. 4 ABSORPTION SPECTRUM OF LYMPHOCYTO-MONOPROSKINESIN IN WATER AT 20°C. EXTINCTION SCALE (0-100) E = 0-2 AT A LIGHT PATH d = 1 cm.

FIG. 5 ABSORPTION SPECTRUM OF MONOCYTO-GRANULOTAXIN IN WATER AT 20°C. EXTINCTION SCALE (0-100) E = 0-2 AT A LIGHT PATH d = 1 cm.

FIG. 6 ABSORPTION SPECTRUM OF GRANULOCYTO-MONOTAXIN IN WATER AT 20°C. EXTINCTION SCALE (0-100) E = 0-2 AT A LIGHT PATH d = 1 cm.

ABSORPTION SPECTRUM OF MONOCYTO-EOSINOTAXIN IN WATER AT 20°C. EXTINCTION SCALE (0-100) E = 0-2 AT A LIGHT PATH d = 1 cm.

STANDARD PYROGEN TEST ACCORDING TO EUR. PHARMACOPOEIA 1975, VOL. II: RECTAL TEMPERATURE OF A RABBIT PRIOR TO (V, A), DURING (*) AND AFTER (P) INTRAVENOUS APPLICATION OF 10 μg LYMPHOCYTO-MONOAPOKINESIN (LMAK) WHICH CORRESPONDS TO ABOUT 0.4 nmol LMAK/kg ANIMAL.

STANDARD PYROGEN TEST ACCORDING TO EUR. PHARMACOPOEIA 1975, VOL. II: RECTAL TEMPERATURE OF A RABBIT PRIOR TO (V, A), DURING (*) AND AFTER (P) INTRAVENOUS APPLICATION OF 10 μg LYMPHOCYTO-MONOAPOKINESIN (LMAK) WHICH CORRESPONDS TO ABOUT 0.4 nmol LMAK/kg ANIMAL.

STANDARD PYROGEN TEST ACCORDING TO EUR. PHARMACOPOEIA 1975, VOL. II: RECTAL TEMPERATURE OF A RABBIT PRIOR TO (V, A), DURING (*) AND AFTER (P) INTRAVENOUS APPLICATION OF 10 μg LYMPHOCYTO-MONOAPOKINESIN (LMAK) WHICH CORRESPONDS TO ABOUT 0.4 nmol LMAK/kg ANIMAL.

REFERENCE 2 nmol/l 10 nmol/l 20 nmol/l

NEGATIVE CHEMOKINETIC EFFECT OF HIGHLY PURIFIED MONOCYTO-GRANULOAPOKINESIN (MGAK) ON PORCINE NEUTROPHIL GRANULOCYTES: INHIBITION OF GRANULOCYTE EMIGRATION FROM GLASS CAPILLARIES.

FIG. 9

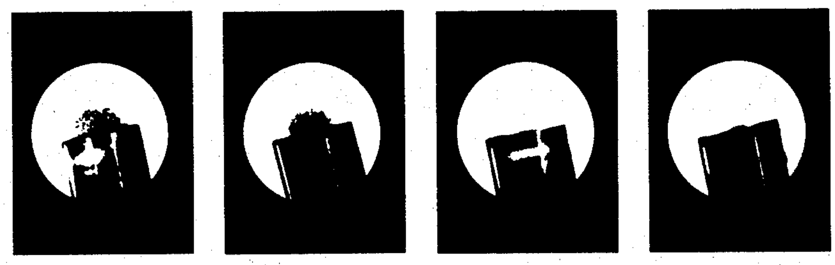

REFERENCE 2 nmol/l 10 nmol/l 20 nmol/l

NEGATIVE CHEMOKINETIC EFFECT OF HIGHLY PURIFIED LYMPHOCYTO-MONOAPOKINESIN (LMAK) ON PORCINE MONOCYTES (MACROPHAGES): INHIBITION OF MONOCYTE EMIGRATION FROM GLASS CAPILLARIES

FIG. 10

LEUCOCYTE - DERIVED SOLUTES
ATTRACTING NEUTROPHIL LEUCOCYTES

CHEMICAL ATTRACTION (CHEMOTAXIS) OF PORCINE NEUTROPHIL GRANULOCYTES BY HIGHLY PURIFIED MONOCYTO-GRANULOTAXIN (MGT) FROM MITOGEN-STIMULATED PORCINE MONOCYTES (TEST SYSTEM: FILTER-TECHNIQUE).

LEUCOCYTE - DERIVED SOLUTES
ATTRACTING MONONUCLEAR LEUCOCYTES

CHEMICAL ATTRACTION (CHEMOTAXIS) OF PORCINE MONOCYTES (MACROPHAGES) BY HIGHLY PURIFIED GRANULOCYTO-MONOTAXIN (GMT) OF PORCINE GRANULOCYTES (TEST SYSTEM: FILTER TECHNIQUE).

LEUCOCYTE - DERIVED SOLUTES
ATTRACTING EOSINOPHIL LEUCOCYTES

CHEMICAL ATTRACTION (CHEMOTAXIS) OF PORCINE EOSINOPHIL LEUKOCYTES BY HIGHLY PURIFIED MONOCYTO-EOSINOTAXIN (MET) FROM MITOGEN-STIMULATED PORCINE MONOCYTES (TEST SYSTEM: FILTER TECHNIQUE).

CHEMOKINESINS AND CHEMOTAXINS OF LEUKOCYTES AND INFLAMED TISSUES

BACKGROUND OF THE INVENTION

Chemokinesins and chemotaxins of leukocytes are endogenous chemical self-components which activate and regulate the processes of emigration of leukocytes from the blood stream and their accumulation in tissue in inflammatory processes.

Local injuries in tissue cause an inflammatory reaction. The inflammatory reaction is defined as process which begins with a sublethal tissue injury and ends with complete destruction or complete healing of the tissue.

The inflammatory reaction comprises numerous biological signal processes. Cells and mediators of inflammation belong to the structural equivalents of this cybernetic loop of the information network of the inflammatory process. Like the classical hormones of endocrine glands, the inflammatory mediators are also substances which are present in only minute concentrations as traces in tissues and in blood. For example, it can be shown that a dividing cell can maintain only up to 5,000 of such mediator molecules in a steady state equilibrium in its surrounding medium.

Many different cell types participate in the biological information network. In particular, they include the different tpyes of leukocytes which accumulate at the reaction site of inflammation in the tissue. These leukocyte types can be subdivided into the following groups: Neutrophils, eosinophils, basophils, monocytes (macrophages), lymphocytes and the different types of juvenile forms of these cells.

The complex biosynthesis from a common precursor form of these cells takes place in the bone marrow. After cell formation, they are stored in the bone marrow as juvenile or mature cell forms. From their primary (so-called poietic) storage pools in the bone marrow they are mobilized and recruited as blood leukocytes into the blood stream, when necessary. The emigration of leukocytes from the blood stream and their accumulation at the reaction site of tissue injury is not a passive process. It is an active process and occurs in well-defined emigration sequences of specific leukocyte populations. Therefore, time-dependently, either different homogenous or mixed populations of leukocytes may accumulate at the reaction site of inflammation.

Inflammatory mediators are soluble chemical substances which participate in the activation and regulation of the body's defence-system as carriers of specific information. They are formed at the reaction site of inflammation by humoral or cellular mechanisms. The transmission of their specific information occurs systemically or locally to neighbour or remote target cells. The mode of action of inflammatory mediators is often similar to that of the hormones of known endocrine glands.

The possible existence of inflammatory mediators with defined structure was first shown by Sir Thomas Lewis (1927) "The Vessels of the Human Skin and their Responses", Shaw, London. He showed that the so-called "triple response" can be mimicked by histamine, a substance of known structure. Today, many different kinds of inflammatory mediators are known. Inflammatory mediators can be simple or complex organic molecules, such as histamine, serotonin, prostaglandins, prostacyclins, thomboxans, leukotriens, etc.

Chemotaxis is a reaction, by which the direction of locomotion of cells or organisms is determined by chemical substances in their environment. This definition shows that chemotaxis is not a specific ability of leukocytes alone, but is a basic property of all living organisms.

Apart from directional locomotion to chemical stimuli (chemotaxis), cells can also be influenced chemically in their motility (chemokinesis). This may result in an inhibition or a promotion of their random locomotion. Accordingly, chemokinesis is a reaction by which the motility of cells or organisms migrating randomly randomly is determined by chemical substances in their environment; see W. Rothert, Flora, vol. 88, 1901, p. 371-421.

Positive and negative changes in the migration trace of a cell may result from alterations in cellular speed, probability and frequency of migration or tumbling and direction of locomotion. These changes in the random migration trace are called positive or negative chemokinesis. If all these changes cancel out each other, the substance investigated has an indifferent chemokinetic activity.

Chemotaxis and chemokinesis of leukocytes (leukotaxis and leukokinesis) can be objectively measured and differentiated only in well defined in vitro test systems. In vivo, such a measurement or differentiation of chemotaxis and chemokinesis is possible only with laborious and ingeneous device systems; see I. K. Buckley, Exp. Mol. Pathology, vol. II. p. 402 to 417.

Therefore, for a long time, a main research problem was the development of reproducible in vitro assay systems for chemokinesis and chemotaxis of leukocytes. The assessment in vitro occurs either by direct microscopic observation of single migration steps of single cells concomitantly to a measurement of locomotion speed of cells migrating in a concentration equilibrium or along a concentration gradient of the substance to be investigated. The results obtained have then to be examined as to whether or not they conform to or deviate from basic relations of random walk theory; see S. C. Peterson, P. B. Noble, Biophys. J. vol. 12, (1972), p. 1048 to 1055. When they conform to basic relations of random walk theory, the type of migration is called chemokinesis; If they deviate from the relations, the type of migration of cells is called chemotaxis. Another test system for chemokinesis and chemotaxis has been developed by S. V. Boyden in the form of a filter assay system consisting of a two compartment chamber. Today, many modifications of this assay system exist. In principle, the migration of many cells through the pores of a filter is measured; see J. H. Wissler et al., Eur. J. Immunol. vol. II, p. 90-96.

An alternative test system for the measurement of negative chemokinetic activity of substances uses the inhibition of cell emigration from glass capillaries; see A. R. Rich and M. R. Lewis, Bull. John Hopkins Hosp., vol. 50 (1932), p. 115 to 131. This inhibition is reversible, if the cells after the assay can be shown to be functionally viable. This functional viability has to be demonstrated in a further assay system, i.e. whether or not they are still chemotactically responsive and motile. If the substances investigated are cytotoxic and therefore, the inhibition of migration is positive, then the result of this second assay system is negative: The observed migration inhibition was not caused by reversible chemokinetic activity of the substance under investigation but the motility of the cells was inhibited by irreversible cytotoxic actions and loss in the function of the cells.

V. Menkin, Biochemical Mechanisms in Inflammation, Charles C. Thomas, Springfield, Ill., 1956 has shown that soluble mediators are contributory factors in mechanisms which induce the emigration of blood leukocytes from blood vessels and their accumulation in tissues. He isolated a crystallizable preparation of substances from inflammatory exudates whose nature has not been characterized in detail. However, with this preparation, he could induce an accumulation of leukocytes in tissues. It has been assumed, however, that contamination with bacterial endotoxins and other exogenous substances in the preparations obtained have contributed to the different types of activities displayed. Such exogenous substances, like endotoxins have a strong indirect biological action on blood plasma or blood cells. It is known that on the one hand, endotoxins may activate blood plasma protein systems, such as kinine and complement protein systems. On the other hand, they have a mitogenic effect on mononuclear leukocytes (B-cell mitogens); see Anderson et al. J. Exp. Med. 137 (1973), p. 943 to 953.

As a result of these findings, humoral serum protein preparations with chemotactic and/or chemokinetic activity on leukocytes have been prepared. However, these preparations have been neither molecularly homogeneous nor have they been biologically specific in their action. Nor have they been characterized in detail; see P. C. Wilkinson (ed.) Chemotaxis and Inflammation, Ch. Livingstone, Edinburgh (1974).

Thus, some of these protein preparations also induce a leukocytosis reaction in vivo; see B. Damerau et al., Naunyn-Schmiedberg's Arch. Pharmacol. 302 (1978), p. 45 to 50. Detailed investigations of the mechanisms of formation of humoral chemotaxins for leukocytes derived from serum-proteins have shown their relationship with anaphylatoxin activity which was detected by Friedberger in 1910; see J. A. Jensen, in Ingram, D. G., (ed.): Biological Activities of Complement, Karger, Basle, (1972), p. 132 to 157.

More recently, using modern chromatographical preparation techniques, such biological active humoral trace proteins could be isolated and characterized in molcularly homogenous, crystalline and chemotactically acting form after about 5,000 to 20,000 fold purification; see J. H. Wissler, Eur. J. Immunol., vol. II, (1972), p. 73-96. These protein preparations have neither a leukokinetic activity nor can they mobilize and recruit leukocytes from the bone marrow into blood circulation.

It is these molecular-biological properties, i.e. the distinct cell and action specificity, in which the natural humoral leukotaxin protein preparations prepared and highly purified from contact-activated serum basically differ from less purified natural and, especially, from synthetic low-molecular peptide leukotaxins (formylmethionyl derivatives etc.). Taxis, kinesis, adhesion, aggregation and, in addition, phagocytosis of leukocytes are concomitantly and indiscriminately induced by such preparations and by the synthetic peptide.

Consequently, it has been postulated that a common receptor in the cell membrane of leukocytes exists which indiscriminately transmits information for taxis, kinesis, adhesion, aggregation and phagocytosis to the cell.

However, further investigation with highly purified, specifically acting natural mediators show that these postulates are not in conformity with reality. This can be directly demonstrated by comparing the activity of the low-molecular synthetic peptide with the highly purified humoral, natural cell and reaction-specific leukotaxin preparations. While the synthetic peptides indiscriminately activate cells to chemotaxis, chemokinesis, adhesion and aggregation, the specific natural humoral leukotaxin protein preparations only induce directional locomotion (chemotaxis) of leukocytes, without influencing their chemokinesis, adhesion, aggregations or phagocytosis responses.

All the mentioned and described preparations for influencing the chemokinesis and chemotaxis of leukocytes are humoral, serum protein-derived chemical substances. In addition, the existence of cellular (cell-secreted) chemotaxins has been shown. Furthermore, a migration-inhibiting activity of cellular origin has been found ("migration-inhibiting factor", MIF). However, the preparations which cause these activities have neither been characterized in detail nor they they been obtained in a form acting in a biologically specific manner. Surveys on the variety of demonstrated biological activities are given in B. R. Bloom and J. R. David (ed.) "In Vitro Methods in Cell-mediated and Tumor Immunities", Academic Press, New York, 1976 and by J. I. Gallin and P. G. Quie (eds.) "Leukocyte Chemotaxis: Methods, Physiology and Clinical Applications", Raven Press, New York 1978.

The literature reveals that cellular chemokinesins have not been investigated or demonstrated so far. The migration inhibition activity of the MiF preparation has not been clearly distinguished from chemotactic activities. As far as they have been investigated, none of these preparations shows biological specificity. For instance, one chemotatic activity is said to be identical to the transfer factor activity; see J. I. Gallin and P. G. Quei, loc. cit. Moreover, it is largely unknown whether or not such cellular activities can be differentiated from serum-derived humoral activities.

It is therefore a primary object of this invention to provide a new class of cellular chemotoxins and chemotropins and leukocytes.

It is another object of this invention to provide a new class of cellular chemokinesins and chemotaxins from leukocytes in highly purified form.

It is another object of this invention to provide a new class of cellular chemokinesins and chemotaxins from leukocytes in physical quantities for practical use.

It is another object of this invention to provide a new class of chemokinesins and chemotaxins from leukocytes, which represent biologically specific, active and naturally acting mediators for the promotion of the motility or the directional migration of leukocytes.

It is another object of this invention to provide a new class of chemokinesins and chemotaxins from leukocytes, which are suitable for specifically influencing inflammatory processes in mammalian (e.g. human) organisms.

It is still another object of this invention to provide a process for producing said obtaining a new class of chemokinesins and chemotaxins from leukocytes in an economical, biotechnically useful and relatively simple manner.

It is still another object of this invention to provide a process for producing and obtaining a new class of chemokinesins and chemotaxins from leukocytes in a highly purified, molecularly homogenous form and in physical quantities for practical use.

It is still another object of this invention to provide a pharmacetical composition for specifically influencing inflammatory processes in the body of mammalians.

These and other objects and advantages of the present invention will be evident from the following description of the invention.

SUMMARY OF THE INVENTION

The subject matter of the invention are chemokinesins and chemotaxins of leukocytes and inflamed tissue, which are characterized by the following properties:

(a) biological activities in vivo and in vitro:
  - selective reversible influence on the motility of leukocytes (chemokinesis) or selective chemical attraction of leukocytes (chemotaxis) in vitro;
  - they are substantially free of other biological effects;

(b) physico-chemical properties:
  - soluble in aqueous media including in 15% ethanol at a pH value of at least 4.0 to 10;
  - insoluble in an ammonium sulfate solution at 90% saturation (3.6 mol/l);
  - electrophoretic migration in acrylamide matrices at a pH of 7.40 is anodic;
  - they absorb reversibly in structure and biological activity on anion and cation exchangers, calcium phosphate gel and hydroxyapatite and can be subjected in native form to volume partition chromatography.

The chemokinesins and chemotaxins of leukocytes and inflamed tissue which are evaluated for the first time and obtained in highly purified form in this invention are further characterized by the fact that they are substantially free of other biological effects. More particularly the chemokinesins and chemotaxins of the invention do not show:
  - mobilization of adult and juvenile leukocytes from the bone marrow (leukocytosis or leftward shift reaction);
  - spasmogenic effects on striated muscles;
  - endotoxin contents and endotoxin-like or similar activities;
  - significant pyrogenic effects in vivo;
  - lysis effects in vitro on erythrocytes, thrombocytes and leukocytes;
  - direct chemotropic mitogen effects on blood vessel cells;
  - mitogenic effects on leukocytes;

DETAILED DESCRIPTION OF THE INVENTION

Figure 1:
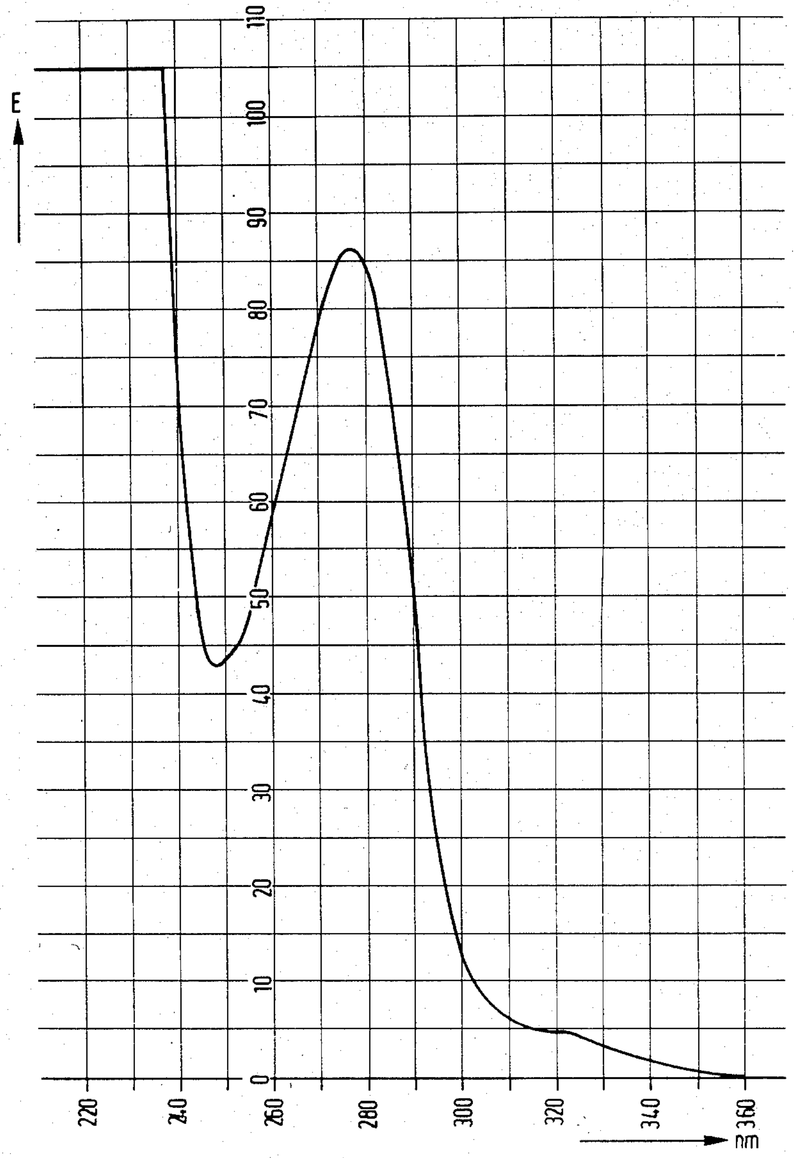

The chemokinesins and chemotaxins of the invention have typical protein proteins and protein reactions (folin and biuret reactions). Their melting points is at approximately 200° C. (decomposition in an air and oxygen-free atmosphere). The chemokinesins and chemotaxins of the invention are structurally (antigenically) distinguishable from humoral chemokinesins and chemotaxins.

The chemokinesins and chemotaxins of the invention are celluar inflammatory mediators with topobiochemically and biologically specific activity. Where in the following text both groups of substances are meant, they are referred to as "mediator proteins" for the sake of brevity. It is their biological task to regulate the emigration of mature and juvenile blood leukocytes. The mediator proteins are not normal independent blood or serum components. Apart from many other hormones and mediators, they are formed in vitro in leukocyte cultures or in vivo upon accumulation of leukocytes at the site of inflammation. From this it is apparent that the mediator proteins of the invention differ in many of their biological and chemical properties from structural and functional properties of the bacterial endotoxins. An $LD_{50}$ value cannot be measured, since no lethal effects have been observed even with doses 10,000 times the amount of the physiologically active threshold dose.

The activity of the mediator proteins of the invention is measured in three different test systems. The first test is the direct microscopic observation of individual leukocytes and quantification of chemically-induced changes of the parameters of the cell migration trace. These are speed, frequence, direction and length of the migration steps of individual leukocytes. Said parameters are compared by means of the random walk theory under the influence of the substances to be tested; see S. C. Peterson and P. B. Noble, loc. cit. The test is performed with and without the concentration gradient of the substance to be tested. If all parameters satisfy the random walk theory, no chemotaxis is involved. The type and intensity of a possible chemokinesis are decided by the parameters. In the second test, chemokinesis and chemotaxis are determined by statistically measuring the migration of leukocyte populations. The negative chemokinesis of leukocytes is statistically measured by the third test based on the inhibition of the emigration of leukocyte populations from capillaries; see A. R. Rich and M. R. Lewis, loc. cit.

The chemokinesins can be divided into two main groups. According to Rothert, loc. cit., substances which reduce the random locomotion of the cells are called negative chemokinesins or apochemokinesins. If the random locomotion of the cells is increased, positive or proschemokinesins are involved. Where the activity is directed to a cell type in a selective or specific manner, the mediator proteins are named by definition, for instance "monapokinesin", "mono-proskinesin" or ∓granulo-apokinesin" and "granulo-proskinesin". This means that the corresponding chemokinesin reduces or increases the random migration of monocytes or granulocytes.

Moreover, the chemokinesins of the invention can stem from different leukocyte types. This is also taken into consideration in the name by defintion.

Accordingly, the lymphocyto-monoapokinesin (LMAK) is a chemokinesin which is produced by lymphocytes and specifically reduces the statistic locomotion of monocytes (macrophages). The monocyto-granuloapokinesin (MGAK) is a chemokinesin which is produced by monocytes and specifically reduces the locomotion of granulocytes. Analogously, the monocyto-granuloproskinesin (MGPK) is a protein which is produced by monocytes and specifically increases the random locomotion of granulocytes. The lymphocyto-monoproskinesin (LMPK) is a chemokinesin which is produced by lymphocytes and specifically increases the locomotion of monocytes.

Apart from or in addition to the above-mentioned properties which the mediator proteins of the invention have in common, the LMAK has the following special properties:

(a) biological effects:
  - specific reversible lowering of the motility of macrophages (monocytes) in vitro;

effective threshold dose in vitro: <2 nmol/l;
(b) physico-chemical properties:
molecular weight of the native protein (primary structure): approximately 14,000 dalton;
absorption spectrum (UV, visible and near IR-range) as given in FIG. 1;
extinction coefficients according to the following Table I:

TABLE I

| Wave length, nm | $E_{1\ mg/ml,\ 1\ cm\ (H_2O,\ 20^\circ\ C.)}$ + 6% |
|---|---|
| 248 (min) | 0.43 |
| 260 | 0.59 |
| 277 (max) | 0.86 |
| 280 | 0.84 |
| 290 | 0.47 |
| 400-1000 | 0 |
| $E_{280}/E_{260}$ | 1.42 |

Figure 2:
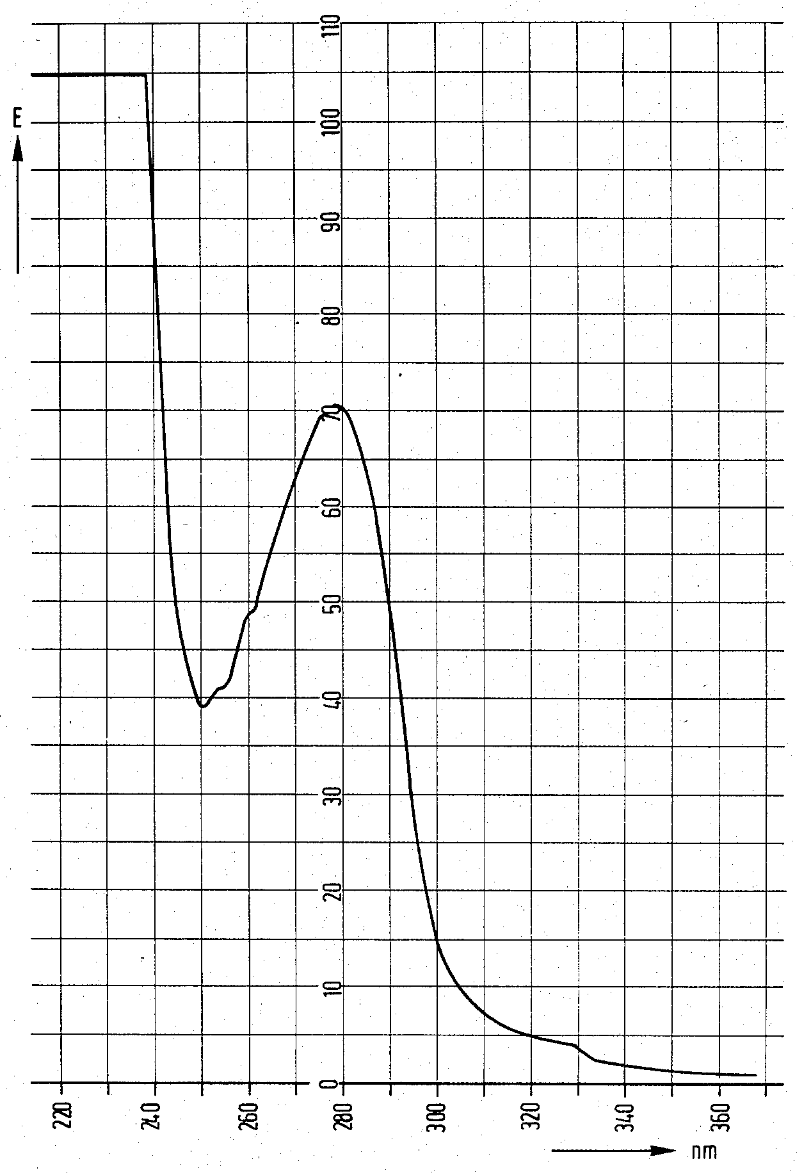

Apart from or in addition to the above-mentioned properties which the mediator proteins of the invention have in common, the MGK has the following special properties:
(a) biological activities:
specific reversible lowering of the motility of granulocytes in vitro;
effective threshold dose in vitro: <1 nmol/l;
(b) physico-chemical properties:
molecular weight of the native protein (primary structure): approximately 9,000 dalton;
no protein quaternary structure in the form of physically bound peptide subunits: each of the native proteins consists of only one peptide unit;
constant temperature coefficient of solubility in ammonium sulfate solutions between −10° C. and +50° C.;
absorption spectrum (UV, visible and near IR-range) according to FIG. 2;
extinction coefficient according to the following Table II:

TABLE II

| Wave length, nm | $E_{1\ mg/ml,\ 1\ cm\ (H_2O,\ 20^\circ\ C.)}$ + 6% |
|---|---|
| 249 (min) | 0.39 |
| 260 | 0.48 |
| 278 (max) | 0.71 |
| 280 | 0.70 |
| 290 | 0.48 |
| 400-1000 | 0 |
| $E_{280}/E_{260}$ | 1.45 |

Apart from or in addition to the above-mentioned properties which the mediator proteins of the invention have in common, the MGPK has the following special properties:
(a) biological activities:
specific reversible increase of the motility of granulocytes in vitro;
effective threshold dose in vitro: <2 nmol/l;
(b) physico-chemical properties:
molecular weight of the native protein (primary structure): approximately 16,000 dalton;
absorption spectrum (UV, visible and near IR-range) as given in FIG. 3.;
extinction coefficient according to the following Table III:

TABLE III

| Wave length, nm | $E_{1\ mg/ml,\ 1\ cm\ (H_2O,\ 20^\circ\ C.)}$ + 6% |
|---|---|
| 251 (min) | 0.36 |

TABLE III-continued

| Wave length, nm | $E_{1\ mg/ml,\ 1\ cm\ (H_2O,\ 20^\circ\ C.)}$ + 6% |
|---|---|
| 260 | 0.42 |
| 278 (max) | 0.56 |
| 280 | 0.54 |
| 290 | 0.35 |
| 400-1000 | 0 |
| $E_{280}/E_{260}$ | 1.29 |

Apart from or in addition to the above-mentioned properties which the mediator proteins of the invention have in common, the LMPK has the following special properties:
(a) biological activities:
specific increase of the motility of macrophages (monocytes) in vitro;
effective threshold dose in vitro: <10 nmol/l;
(b) physico-chemical properties:
molecular weight of the native protein (primary structure): approximately 22,000 dalton;
absporption spectrum (UV, visible and near IR-range) as given in FIG. 4;
extinction coefficient according to the following Table IV:

TABLE IV

| Wave length, nm | $E_{1\ mg/ml,\ 1\ cm\ (H_2O,\ 20^\circ\ C.)}$ + 6% |
|---|---|
| 249 (min) | 0.29 |
| 260 | 0.40 |
| 279 (max) | 0.65 |
| 280 | 0.65 |
| 290 | 0.49 |
| 400-1000 | 0 |
| $E_{280}/E_{260}$ | 1.62 |

The above-described chemokinesins of the invention, LMAK, MGAK, MGPK and LMPK are further characterized by the fact that they substantially do not display the following biological activities:
capillary permeability-enhancing activity in the skin test;
spasmogenic activity on smooth muscles;
chemotaxis of leukocytes in vitro;
phagocytosis-stimulating effects on leukocytes in vitro;
apparent shock or other systemically detrimental effects of the immediate or protracted type on the intact organism of mammals in vitro.

Furthermore, MGPK and LMPK do not show phlogistic activity in situ.

The chemotaxins of the invention are analogously named by definition after the specific leukocyte type on which they act and after that by which they are produced. Thus monocyto-granulotaxin (MGT) is a chemotaxin which is produced by monocytes and specifically influences the directional migration of granulocytes. Granulocyto-monotaxin (GMT) is a chemotaxin which is produced by granulocytes and specifically influences the directional migration of monocytes (macrophages). Finally, monocyto-eosinotaxin (MET) is a chemotaxin, which is produced by monocytes and specifically influences the directional migration of eosinophil leukocytes.

Figure 5:
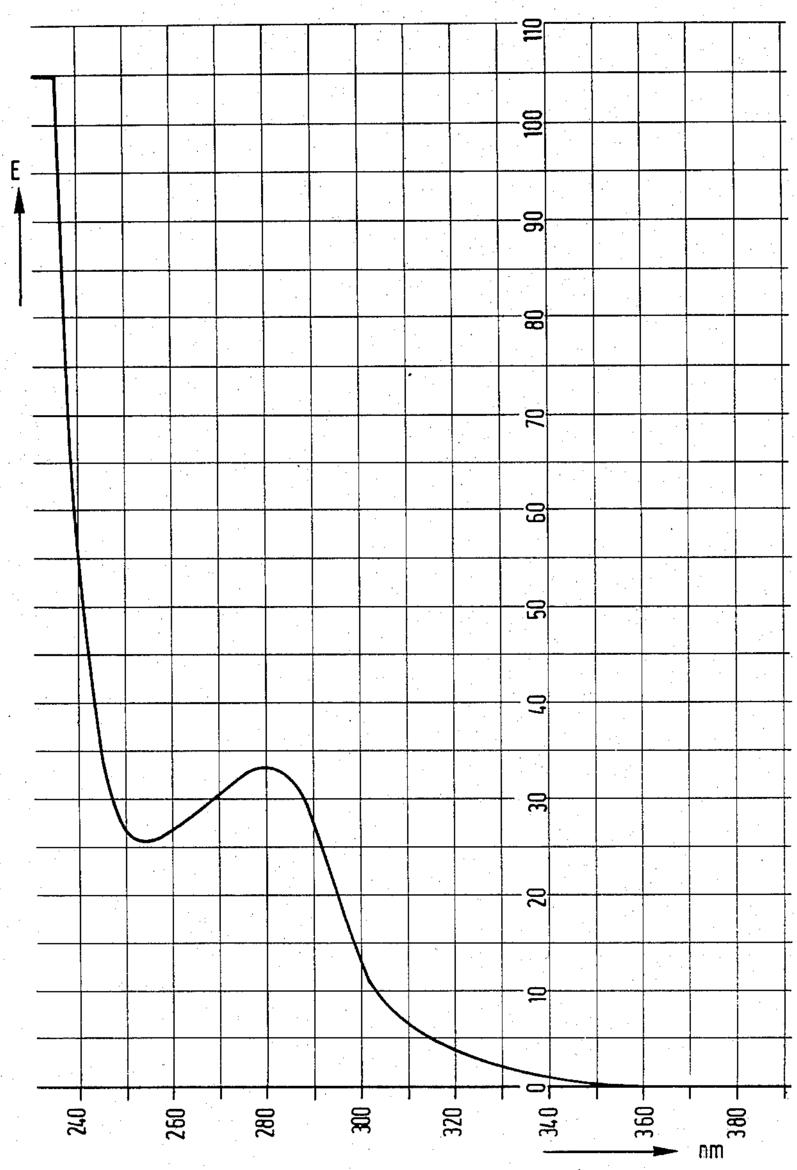

Apart from or in addition to the above-mentioned properties which the mediator proteins of the invention have in common, MGT has the following special properties:
(a) biological activities:

chemical attraction of neutrophilic granulocytes in vitro;

accumulation of neutrophilic leukocytes in situ with indirect cell-induced angiogenesis and inflammation reaction;

effective threshold dose in vitro: <0.5 nmol/l;

(b) physico-chemical properties:

molecular weight of the native protein (primary structure): approximately 11,000 dalton;

absorption spectrum (UV, visible and near IR-range) as given in FIG. 5;

extinction coefficient according to the following Table V:

TABLE V

| Wave length, nm | $E_{1\ mg/ml,\ 1\ cm\ (H_2O,\ 20^\circ\ C.)} + 6\%$ |
|---|---|
| 253 (min) | 0.51 |
| 260 | 0.54 |
| 278 (max) | 0.66 |
| 280 | 0.66 |
| 290 | 0.54 |
| 400-1000 | 0 |
| $E_{280}/E_{260}$ | 1.23 |

Figure 6:
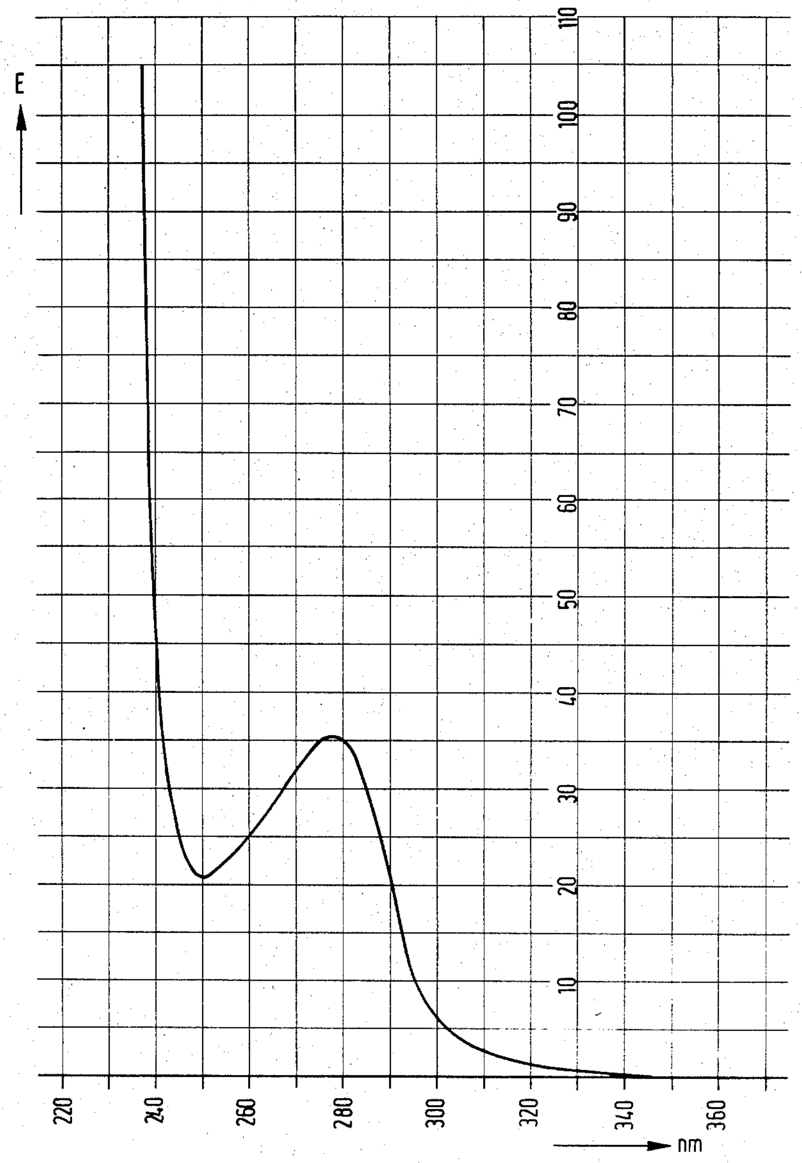

Apart from or in addition to the above-mentioned properties which the mediator proteins of the invention have in common, GMT has the following special properties:

(a) biological activities:

chemical attraction of macrophages (monocytes) in vitro;

accumulation of monocytic leukocytes in situ with indirect, cell-induced angiogenesis and inflammation reaction;

effective threshold dose in vitro: <10 nmol/l;

(b) physico-chemical properties:

molecular weight of the native protein (primary structure): approximately 17,000 dalton;

absorption spectrum (UV, visible and near IR-range) as given in FIG. 6;

extinction coefficient according to the following Table VI:

TABLE VI

| Wave length, nm | $E_{1\ mg/ml,\ 1\ cm\ (H_2O,\ 20^\circ\ C.)} + 6\%$ |
|---|---|
| 249 (min) | 0.36 |
| 260 | 0.43 |
| 278 (max) | 0.60 |
| 280 | 0.59 |
| 290 | 0.34 |
| 400-1000 | 0 |
| $E_{280}/E_{260}$ | 1.37 |

Figure 7:
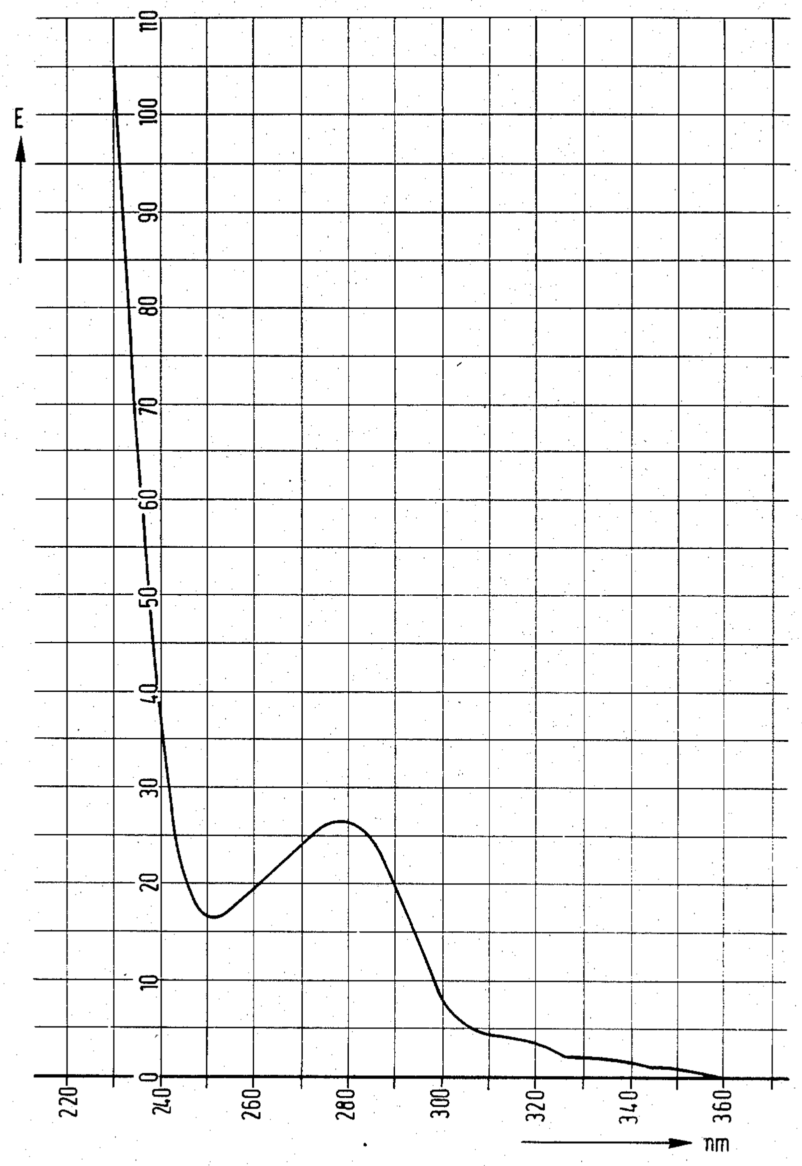

Apart from and in addition to the above-mentioned properties which the mediator proteins of the invention have in common, MET has the following special properties:

(a) biological activities:

chemical attraction of eosinophilic leukocytes in vitro;

accumulation of eosinophilic leukocytes in situ;

effective threshold dose in vitro; <5 nmol/l;

(b) physico-chemical properties:

molecular weight of the native protein (primary structure): approximately 5,000 dalton;

no protein quaternary structure in the form of physically bound peptide subunits: each of the native proteins consists of only one peptide unit;

absorption spectrum (UV, visible and near IR- range) as given in FIG. 7;

extinction coefficient according to the following Table VII:

TABLE VII

| Wave length, nm | $E_{1\ mg/ml,\ 1\ cm\ (H_2O,\ 20^\circ\ C.)} + 6\%$ |
|---|---|
| 252 (min) | 0.33 |
| 260 | 0.39 |
| 277 (max) | 0.53 |
| 280 | 0.53 |
| 290 | 0.39 |
| 400-1000 | 0 |
| $E_{280}/E_{260}$ | 1.36 |

The chemotaxins of the invention, MGT, GMT and MET do not show positive or negative chemokinetic effects on leukocytes in vitro nor apparent shock or other systemically detrimental effects of the immediate or protracted type on the intact organism of mammals in vivo.

Up to non-physiological concentrations of 10 μmol/l, the mediator proteins of the invention have neither leucocytosis-inducing nor phagocytotic or mitosis-stimulating activities on neutrophil, eosinophil and mononuclear leukocytes of man, rabbit, pig, dog, guinea pig or rat. Finally, they have no apparent shock effect at threshold dose nor do they display a pyrogenic activity in rabbits (standardized method by measurement of rectal temperature according to Euro. Pharmacopoeia, vol. II (1975), p. 56 to 59).

FIGS. 1 to 7 show the UV absortion spectra of the highly purified mediator proteins LMAK, MGAK, MGPK, LMPK, MGT, GMT and MET in water at 20° C. and extinction scale (0-100) E=0-2 at a light path d=1 cm.

Figure 8A:
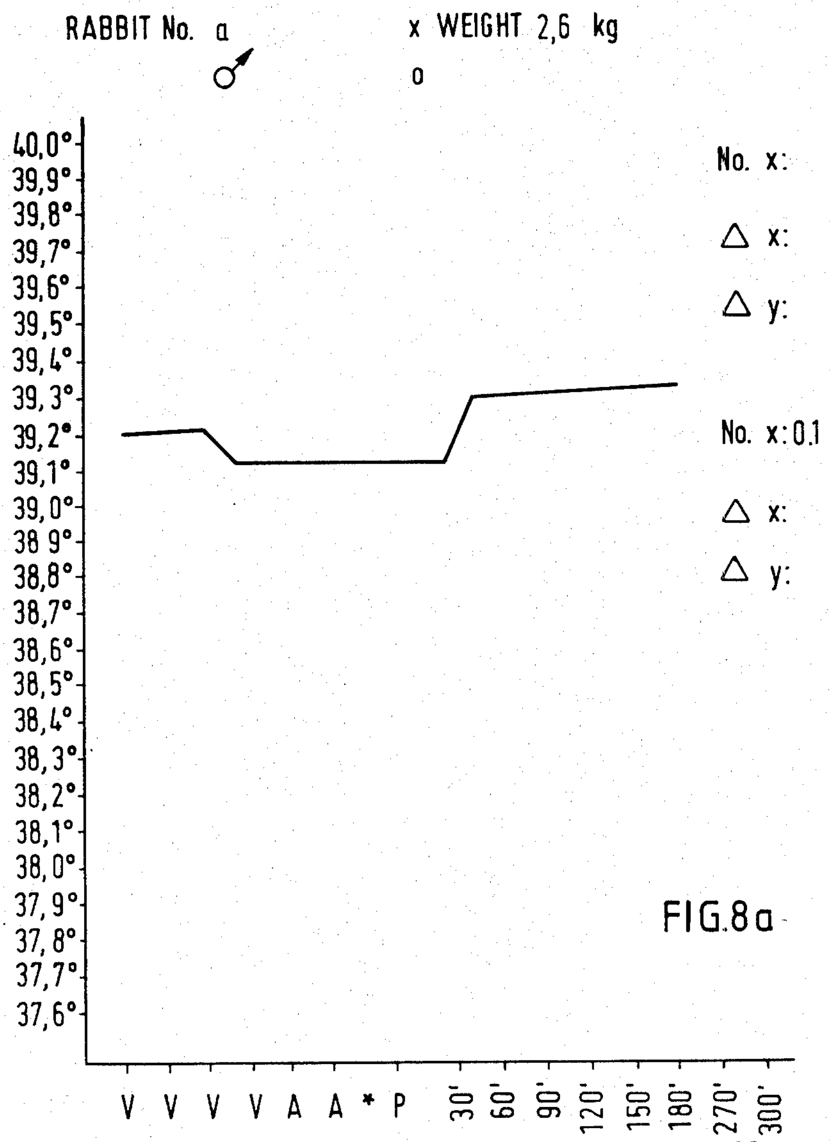
Figure 8B:
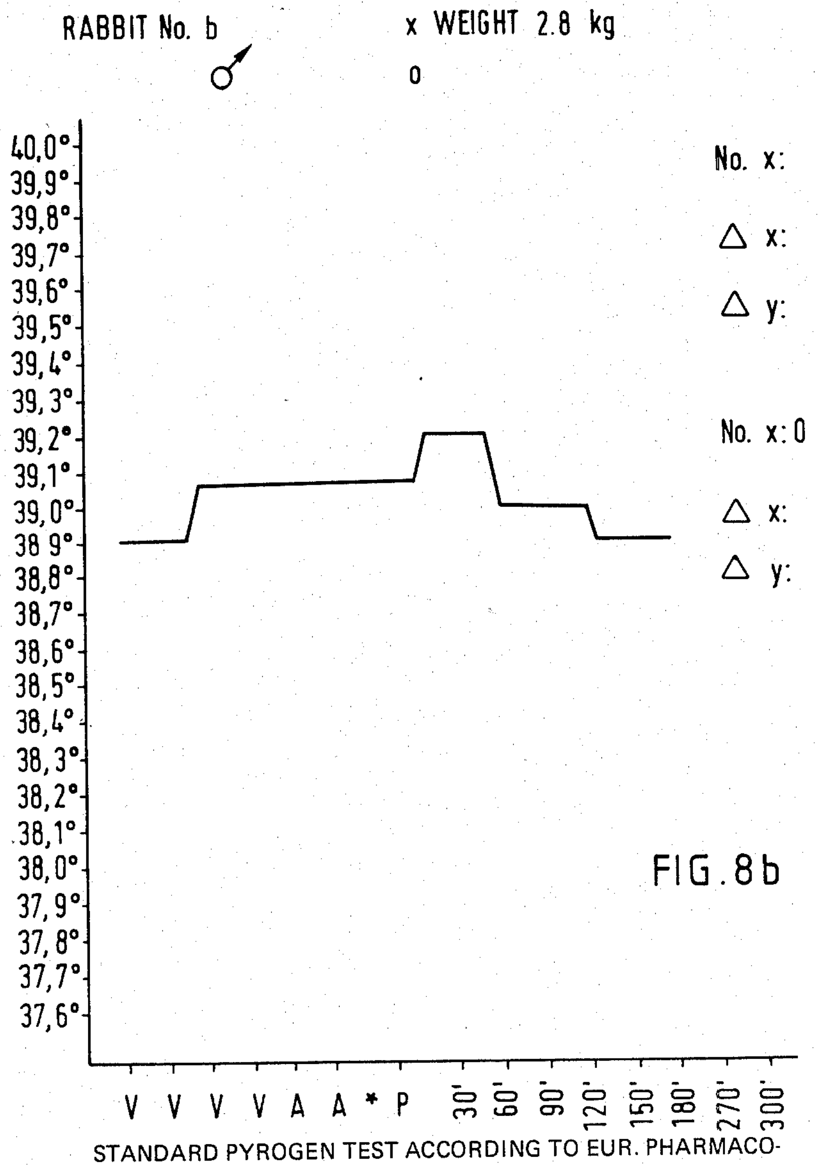
Figure 8C:
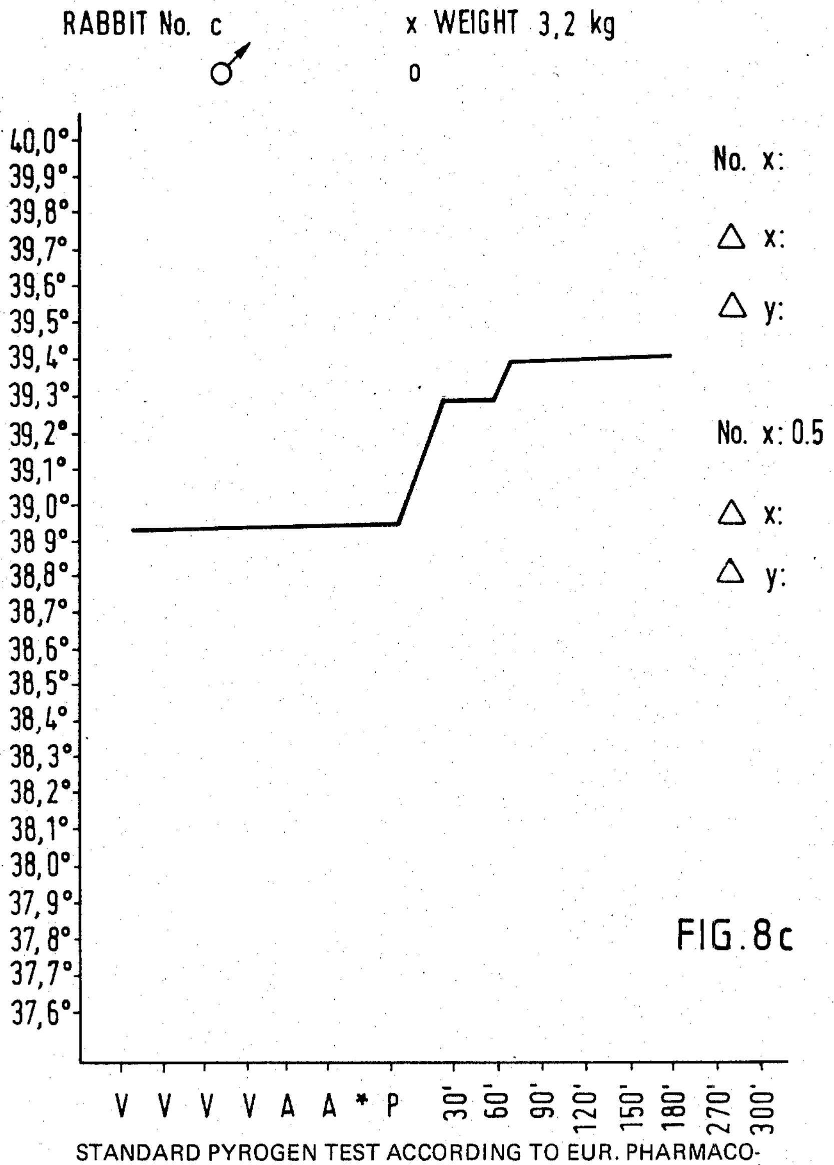

FIG. 8 schematically shows a standard-pyrogen assay according to Europ. Pharmacopoeia, vol. II (1975): The rectal temperature of 3 rabbits (a, b and c) having an average weight of 3 kg is measured prior (V,A), during (*) and shortly after as well as 30 to 180 minutes after intravenous application of 10 μg of LMAK (corresponding to about 0.4 nmol LMAK/kg animal) in 1 ml 0.9 (w/v) % physiological saline.

The 1975 edition of the European Pharmacopoeia, the British (1973) and the American (USP) (1975) Standards allow the designation "pyrogen-free" to be applied to preparations for which the sum of the fluctuations of the rectal temperature in a total of three experimental rabbits does not exceed the value of 2.6° C. and, in particular, is below 1.15° C. The experimental results given in FIG. 8 fullfills these criteria. According to these definitions, the LMAK-preparation is pyrogen-free and without febrile activity. This also applies to the other highly purified mediator protein preparations. This extremely sensitive criterion for contamination of proteins with bacterial endotoxins and other ubiquitous pyrogens demonstrates the great efficacy of the process of the purification of the cellular mediator proteins of the invention. It is an obvious parameter for the biological specificity of the mediator proteins.

Figure 11:
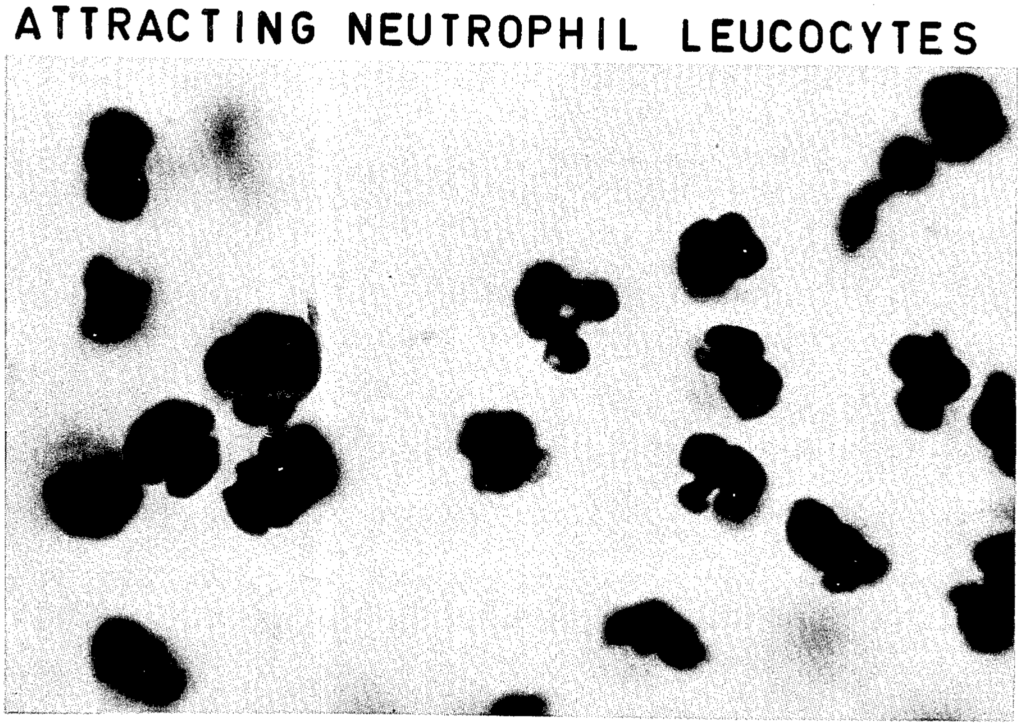
Figure 12:
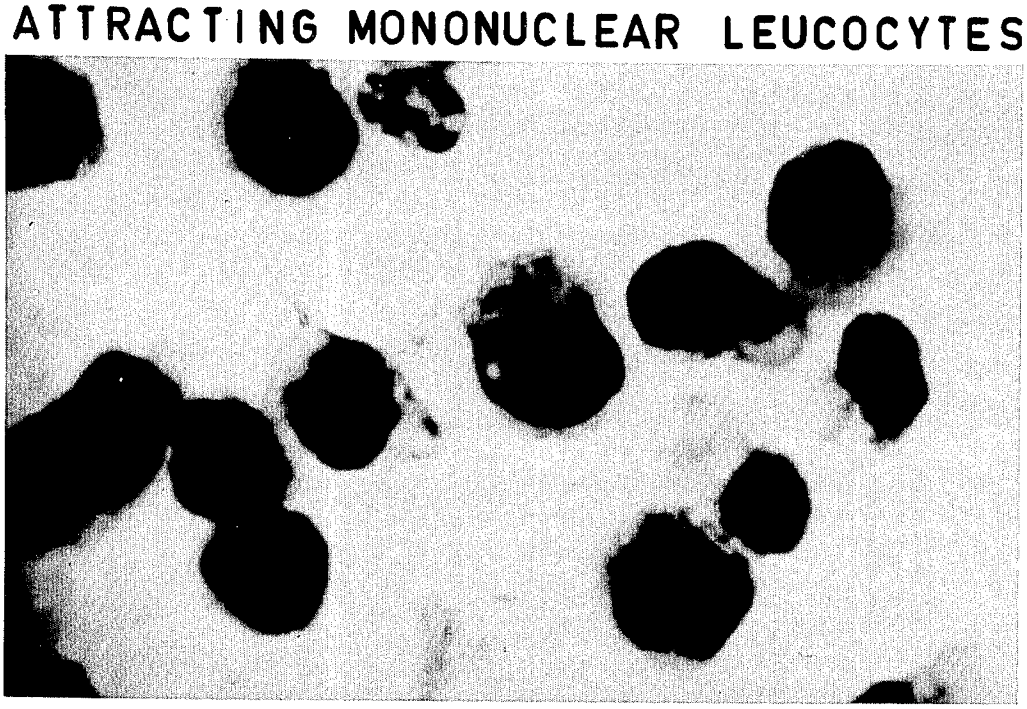
Figure 13:
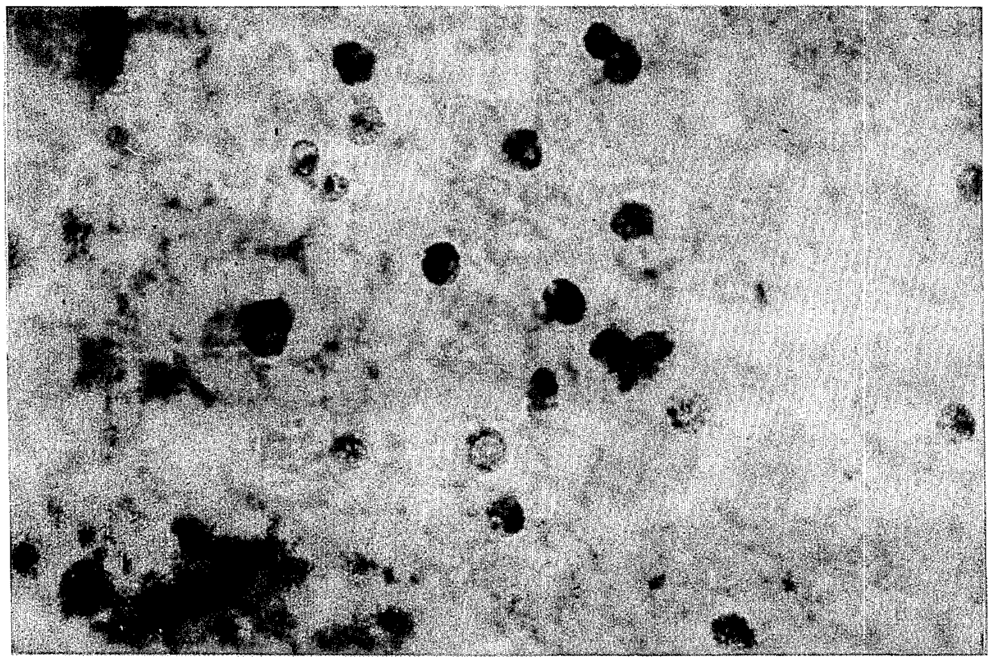

FIGS. 9 to 13 show the negative chemokinetic effect of LMAK and MGAK as well as the chemotactic effect of MGT GMT and MET. FIG. 9 shows the negative chemokinetic effect of LMAK in the form of inhibition of monocyte (macrophage) emigration from glass capillaries. FIG. 10 depicts the same for MGAK. FIG. 11 shows the chemotactic effect of MGT in the form of chemical attraction and directional migration of granulocytes through the pores of a membrane filter. The same is depicted in FIGS. 12 and 13 for GMT and MET for monocytes (macrophages) and eosinophilic leukocytes, respectively.

The mediator proteins prepared and obtained according to the invention are valuable, endogeous substances. They can be used for specifically influencing the defence-state and inflammatory processes of the body, for instance the immune state. They are suitable to specifically influence the emigration and accumulation of leukocytes for inducing desired inflammatory reactions and controlling undesired ones, for instance in tumors. Moreover, the mediator proteins can be used for producing their antibodies which are also suitable to specifically influence leukocyte accumulation processes.

The mediator proteins of the invention are applied locally alone or as a mixture to mammalians, for instance man, in the form of usual pharmaceutical compositions in a daily dose of $>50$ fmol in a concentration of $>1$ nmol/l.

Another subject matter of the invention is a process for the biotechnical preparation and isolation of mediator proteins from leukocytes and from inflamed tissue sites. It is characterized in that either the leukocytes or the inflamed tissue are homogenized; or that leukocytes are cultured and the mediator proteins formed or liberated are isolated from the homogenates or from the supernatant culture solution.

In principle, it is possible to prepare mediators from leukocytes directly without cell cultures. However, such a procedure is not economical: The luekocytes are destroyed by the process; the yields in mediators are low, since their synthesis and secretion is not stimulated prior to isolation; the mediators can be contaminated by intracellular structural constituents of leukocytes. Therefore, in the process of the invention, it is preferred to isolate the mediator proteins from the supernatant solution of the leukocyte culture. In principle, the leukocytes can be cultured in any leukocyte-compatible medium.

For the culture of different cell types, such as bone marrow cells, heart muscle cells or leukocytes, different culture media are known. These media normally are aqueous solutions which contain numerous different compounds. Main constituents of these culture media are salts, sugars and metabolites, amino acids and derivatives, nucleosides, vitamins, vitaminoids, coenzymes, steroids, antibiotics and other additives, such as tensides, heavy metal salts and indicator dyes. Special examples of known culture media are named "HAM", "MEDIUM 199" and "NCTC", see H. J. Morton, In Vitro 6 (1970) p. 89 to 108.

When culturing cells for more than one hour, as in the case of leukocytes, mostly serum (e.g. fetal calf serum or horse serum) is added to the culture medium. The serum constituents are said to be favourable for the maintenance of cellular functions. However, if the serum-containing culture solution is to be subjected to processes for isolating proteins (mediators) which are formed by culturing cells, the preparation of trace protein products is difficult for reasons of the multiplicity of compounds making up the complex mixture of serum added to the culture. In addition, under such conditions, upon addition of serum to a cell culture medium, it is difficult if not at all impossible to recognize the origin of the mediators: It is then an open question whether or not a distinct mediator is of humoral (serum) or cellular (leukocyte) origin and from which species this mediator stems. Thus, the mediator may be derived from the species whose cells have been cultured; or, alternatively, it may be derived from the species from which the added (mostly heterologous) serum stems.

Besides serum-containing culture media, serum-free, synthetic media are also known; see H. J. Morton, loc. cit; I. Hayashi and G. H. Sato, Nature 259 (1976) p. 132–134; N. N. Iscove and F. Melchers, J. Exp. Med. 147 (1978) p. 923–933.

However, these known media likewise have drawbacks for both the culture of cells and for the preparation of the mediators formed from the culture supernatant. The tensides, heavy metal salts and/or dyes contained therein may damage or irreversibly contaminate the trace mediator proteins.

On the other hand, such known serum-free media are devoid of essential constituents which are necessary for maintaining the structural and functional viability of leukocytes. Therefore, none of the culture media known so far can be suitably used for the culture of leukocytes and the biotechnical preparation of cellular trace components, such as mediator proteins.

For the culture of leukocytes, a new, fully synthetic chemically defined culture medium is preferably used. It provides favourable conditions for cell culture and facilitates the preparation and isolation of the cellular mediator proteins from the culture supernatant.

The fully synthetic, chemically defined cell culture medium preferably used in this invention contains the normal groups of compounds, such as salts, sugars, polyols, uronic acids, and derivatives, amino acids and derivatives, nucleosides and nucleoside bases, vitamins, vitaminoids, phtyl derivatives, coenzymes and steroids in aqueous solution. It is characterized in that it additionally contains one or a mixture of several compounds which so far have not been considered for use in cell culture media. These are especially valuable for expression of the life functions, for the proliferation of leukocytes and for promoting their capability to produce mediators. These substances include unsaturated fatty acids, flavanoids, ubiquinone, vitamin U, mevalolactone and L-carnosine.

In prolonged leukocyte culturing, the cell culture medium is preferably used without addition of serum. Instead, it contains at least one defined protein.

In further preferred embodiments of the invention, the synthetic, serum-free cell culture medium used in this invention may contain additional compounds, e.g. polyhydroxy compounds and sugars, amino acids, nucleosides, anionic compounds and/or vitamins which are not common in the known culture media. These compounds are useful in culturing leukocytes. The constituents in the culture medium used in this invention are equilibrated in their ratios so that their concentrations mainly correspond to the natural concentration ranges of the plasma; see Ciba-Geigy AG (editor) (1969) in Documenta Geigy, Wissenschaftliche Tabellen seventh edition, Geigy S. A. Basle.

Preferably, the cell culture medium is free of tensides, heavy metal salts and dye indicators which can damage the cells and may have a detrimental effect on the isolation of the desired cell products.

The exact composition and the properties of the new cell culture medium are described in copending the Patent Application Ser. No. 358,045 filed Mar. 15, 1982 on the basis of West German Patent Application No. P 31 10 559.9.

The cell culture medium with the composition given in Table VIII below is especially preferred in the process of the invention for culturing leukocytes.

The medium is prepared with water of ASTM-1 quality; see ASTM D-1193-70 Standard Specification for Reagent Water 1970; Annual Book of ASTM-Standards, Easton, Md., ASTM 1970. In addition, it is freed from possible endotoxin-contaminations by ultrafiltration on tenside-free membranes with an exclusion limit of 10,000 dalton. The resulting medium is sterilized by filtration on tenside-free membranes with a pore size of 0.2 μm.

TABLE VIII

| No. | Component | mol/l |
|---|---|---|
| 1 | Disodium hydrogenphosphate | 0.8 m |
| 2 | Potassium dihydrogenphosphate | 0.2 m |
| 3 | Potassium chloride | 5.0 m |
| 4 | Sodium chloride | 120.0 m |
| 5 | Sodium sulfate | 0.2 m |
| 6 | D-Glucose | 5.0 m |
| 7 | L-Ascorbic acid (C) | 0.2 m |
| 8 | Choline chloride | 50.0μ |
| 9 | 2-Deoxy-D-ribose | 5.0μ |
| 10 | D-Galactose | 0.5 m |
| 11 | D-Glucurono-γ-lactone | 0.1 m |
| 12 | Glycerol | 50.0μ |
| 13 | Myo-inositol | 0.5 m |
| 14 | Sodium acetate | 0.2 m |
| 15 | Sodium citrate | 50.0μ |
| 16 | Sodium pyruvate | 0.1 m |
| 17 | D-Ribose | 20.0μ |
| 18 | Succinic acid | 0.1 m |
| 19 | Xylitol | 10.0μ |
| 20 | D-Xylose | 20.0μ |
| 21 | Calcium chloride | 2.0 m |
| 22 | Magnesium chloride | 1.0 m |
| 23 | Sodium hydrogencarbonate | 10.0 m |
| 24 | Serum albumin (human) | 7.7μ |
| 25 | L-Asparagine | 0.1 m |
| 26 | L-Glutamine | 1.0 m |
| 27 | Adenosine | 50.0μ |
| 28 | 4-Aminobenzoic acid | 2.0μ |
| 29 | L-Aspartic acid | 0.1 m |
| 30 | D-Biotine (Vitamin H) | 1.0μ |
| 31 | Cytidine | 50.0μ |
| 32 | L-Glutamic acid | 0.1 m |
| 33 | L-Isoleucine | 0.2 m |
| 34 | 5-Methylcytosine | 5.0μ |
| 35 | L-Phenylalanine | 0.1 m |
| 36 | Riboflavine (B2) | 1.0μ |
| 37 | Thymine (5-methyluracil) | 5.0μ |
| 38 | L-Tryptophane | 50.0μ |
| 39 | L-Tyrosine | 0.1 m |
| 40 | Uracil | 5.0μ |
| 41 | Uridine | 20.0μ |
| 42 | L-Leucine | 0.2 m |
| 43 | L-Valine | 0.2 m |
| 44 | Thymidine | 20.0μ |
| 45 | Water | 55.4 |
| 46 | Hydrogen ions (pH 7.1) | 79.4 n |
| 47 | Oxygen (air saturation) | 0.2 m |
| 48 | L-Alanine | 0.2 m |
| 49 | L-Arginine | 0.1 m |
| 50 | D,L-Carnithine chloride (BT) | 50.0μ |
| 51 | L-Carnosine | 5.0μ |
| 52 | L-Cysteine | 0.2 m |
| 53 | L-Glutathione reduced | 3.0μ |
| 54 | Glycine | 0.2 m |
| 55 | L-Histidine | 0.1 m |
| 56 | L-Hydroxyproline | 10.0μ |
| 57 | L-Lysine-HCl | 0.2 m |
| 58 | L-Methionine | 0.1 m |
| 59 | D,L-Mevalolactone | 5.0μ |
| 60 | Nicotinic acid amide | 20.0μ |
| 61 | L-Ornithine-HCl | 50.0μ |
| 62 | D-Ca-pantothenate (B5) | 5.0μ |
| 63 | L-Proline | 0.1 m |
| 64 | Pyridoxal-HCl | 5.0μ |
| 65 | Pyridoxine-HCl (B6) | 2.0μ |
| 66 | Sarcosine | 50.0μ |
| 67 | L-Serine | 0.1 m |
| 68 | Taurine | 0.1 m |
| 69 | Thiamine-HCl (B1) | 5.0μ |

TABLE VIII-continued

| No. | Component | mol/l |
|---|---|---|
| 70 | L-Threonine | 0.2 m |
| 71 | Vitamin B12 | 0.5μ |
| 72 | Vitamin U | 1.0μ |
| 73 | Adenine | 50.0μ |
| 74 | Folic acid (Bc) | 5.0μ |
| 75 | Guanine | 5.0μ |
| 76 | Guanosine | 20.0μ |
| 77 | Hypoxanthine | 5.0μ |
| 78 | Rutin (Vitamin P) | 5.0μ |
| 79 | Xanthine | 5.0μ |
| 80 | Ethanol (60 μl/l) | 1.0 m |
| 81 | Cholesterol | 1.0μ |
| 82 | Ergocalciferol (D2) | 0.5μ |
| 83 | D,L-α-Lipoic acid | 2.0μ |
| 84 | Menadione (K3) | 0.2μ |
| 85 | D,L-α-Tocopherol acetate (E) | 1.0μ |
| 86 | Coenzyme Q 10 ubiquinone 50 | 0.1μ |
| 87 | 3-Phytylmenadione (K1) | 0.2μ |
| 88 | Retinol acetate (A) | 1.0μ |
| 89 | Linolenic acid (F) | 5.0μ |
| 90 | Linoleic acid (F) | 1.0μ |
| 91 | Oleic acid | 5.0μ |
| 92 | Penicillin G | 80.0μ |
| 93 | Streptomycin | 80.0μ |
| 94 | Activator(s) (CON A) | 50.0 n |

Dependent on the type of desired product, either mixed populations of leukocytes or homogenous leukocyte types are cultured. The preparation and culture of leukocytes must be performed under sterile conditions. Culturing is performed for a period sufficiently long to obtain a satisfactory mediator level. A suitable period of time is 10 to 50 hours. Shorter periods result in lower mediator yields and the process is thus not economical. On the other hand, the medium is used up after a culture period of 50 hours and the cells begin to die. An increase of the yield can therefore not be obtained in this case, except in the case of subculturing of cells and renewal of the culture medium.

The leukocytes are cultured at a temperature of about 30° to 42° C., preferably at about 37° C. At lower temperatures the culture process is not satisfactory, while at temperatures of above 42° C. the leukocytes are damaged.

Culturing is carried out at a concentration of about $10^6$ to $5\times10^8$ cells/ml, preferably $10^7$ to $10^8$ cells/ml. At lower cell concentrations the mediator yield per volume unit of the culture solution is too low. With too large culture volumes, the process is not economical. At cell concentrations of above $5\times10^8$ cells/ml, nutrition of the cells in the medium becomes rapidly inefficient.

Culturing can be carried out in normal atmosphere. Preferably increased carbon dioxide partial pressure is maintained during culturing. This pressure can amount to about 10 vol%. 2 vol% are preferred. The oxygen supply to the culture is of great importance. Oxygen can be supplied e.g. by bubbling air through the culture. To avoid contamination of the culture, the air is preferably sterilized and heat-decontaminated, i.e. it is freed of endotoxins and other organic constituents. The cell suspension is stirred or agitated during culturing.

Certain types of the inventive mediator proteins are already obtained in satisfactory yields by normal culture of leukocytes or certain leukocyte types. The GMT, for instance, is obtained in high yields by culturing mixed populations of leukocytes or homogenous populations of granulocytes under the above-indicated conditions.

Other types of mediator proteins of the invention however, are are however only formed in small amounts by normal culture of leukocytes or certain leukocyte types. This applies for instance to the mediator proteins of mononuclear cells.

To produce them in higher yields, it is necessary to stimulate the cells in culture to mitosis. Possible mitosis-inducing influences are the addition of polyvalent mitogens, endotoxin-mitogens and immune reactions on the cell surface of sensitized cells. Examples of suitable mitogens are lectins, in particular those of *Canavalia ensiformis* (Concanavalin A=CON). The mitosis-inducing factor CON is added as a solution to the culture medium.

To terminate culturing, the leukocytes are centrifuged from the supernatant culture solution which is subsequently processed for the resulting mediator proteins. To avoid damaging the cells and thus contamination of the culture solution with cell particles, the culture is centrifuged at relatively low speed, i.e. at about 300 to 400×g. After removal of the major part of the cells from the supernatant, it is expedient to centrifuge the latter again at a higher speed. In this way, the remaining floating particles are removed. The separated leukocytes can either be cultured again, cryo-preserved or used for other biotechnical purposes.

The supernatant culture solution freed from the cells contains the secretion products of the cultured leukocytes. These include the mediator proteins of the invention and a number of other proteins and other substances. Their concentration in the culture solution is approximately within the nanomolar range. Consequently, a yield of about 1 to 10 mg of a defined mediator requires a culture solution volume of about 1,000 l with respect to a 10% recovery after purification. As regards the number of cells to be used, it can be calculated that in view of the molecular efficiency of the cells, about $10^{14}$ leukocytes are necessary for obtaining a quantity of about 100 nmol proteins. This corresponds to about 1 mg of a mediator with the molecular weight of 10,000 dalton. This means that for the isolation of mediators in physical amounts about 50 kg of leukocytes are necessary for the culture. For reasons of availability, leukocytes of man, cow, horse, pig, sheep, dog, cat, rabbit, rat, mouse or guinea pig are preferred. The process described in the German unexamined patent publication DE-OS No. 30 09 126 is especially suitable for the preparation of large amounts of leukocytes; see also J. H. Wissler et al., Hoppe-Seyler's Z. F. Physiol. Chemie, 361 (1980), p. 351 to 352.

Apart form leukocyte cultures, the mediator proteins of the invention can also be obtained from inflamed tissue sites. There, they are formed by the accumulation of leukocytes in the course of inflammatory processes induced by tissue injuries. The inflamed tissue can be obtained in the usual manner and used for the preparation of the mediator proteins. Inflamed tissues are homogenized in buffer solution and soluble constituents or exudates are separated from insoluble structural components by means of centrifugation.

Preferably, inflamed, infarcted heart mucle tissue is used which was formed by ligation of 24 hours of the left anterior descendent branch of the left coronary artery by a transfermoral catheter technique. The leukocyte-containing inflamed heart muscle site is separated at 0° to 4° C. from the remaining non-infracted tissue.

As shown above, the preparation and isolation of the mediator proteins of the invention requires the processing of a very large culture solution volume. Therefore, at the beginning of the purification process effective reduction of the solution volume to be processed is necessary. In addition to the small amounts of the proteins produced, the culture solution contains the mixture of the components of the medium. Preferably in the first step of the purification process a separation of the formed proteins from the medium components with a concomitant reduction of the large volume of aqueous solution is achieved. This can be effected by selective salting-out precipitation of the proteins from the supernatant culture solution, for instance by adding a sulfate or a phosphate. In the following, the salting-out precipitation of proteins is exemplified by adding ammonium sulfate to the culture solution.

By saturation of the supernatant culture solution with ammonium sulfate, a major portion of the proteins formed is precipitated together with serum albumin present as medium component. The proteins precipitated are recovered e.g. by centrifugation. They are then separated into the individual components of the mixture as described below. Thereby, some mediator proteins are obtained. On the other hand, some other mediator proteins are salt-soluble and remain in the supernatant solution of the salting-out precipitation process. This supernatant also contains all soluble components of the medium. It is concentrated and the proteins obtained are processed in the manner described below.

If the protein-containing supernatant culture solution is saturated with ammonium sulfate, a major portion of proteins is precipitated. In this way, a protein mixture is obtained consisting of numerous different proteins. Their separation into the individual protein components is obviously laborious. Therefore, in a preferred embodiment of the inventive process the protein mixture of the supernatant culture solution is already separated into several fractions by the salting-out precipitation step. The separation into several crude protein fractions is possible, since groups of individual proteins precipitate at different ammonium sulfate concentrations. Preferably, in the process of the invention, ammonium sulfate is therefore added stepwise to the culture solution up to a specific degree of saturation. Each fraction contains a group of proteins, the solubility product of which corresponds to the range of salt saturation. Hence, in the process according to the invention a crude separation into groups of proteins can be achieved in this first step by suitable choice of the saturation limits.

For instance, the supernatant culture solution is first brought to a 35% saturation with ammonium sulfate. The protein precipitate obtained is separated off. The 35% saturation of the supernatant solution is then increased to 45% by further addition of ammonium sulfate. A protein precipitate is again formed which is separated off. Thereafter, the 45% salt-saturated supernatant solution is brought to a 90% ammonium sulfate saturation. The protein precipitate formed is again separated off. The supernatant solution of this precipitate is concentrated e.g. by dehydration dialysis or ultrafiltration.

The salting-out precipitation of proteins is preferably carried out at a temperature of about 0° to 10° C., especially of about 0° to 4° C. The subsequent purification steps are performed under the same conditions. The solutions used for the purification have a pH value of between 5 and 9, in particular between 6 and 8. In order to achieve a constant pH-value of the solution, a strong buffer, for instance 0.1 mol/l of phosphate buffer is preferably added prior to the salting-out precipitation. To maintain the redox potential of the proteins, cysteine is preferably added in an amount of 0.001 mol/l to all solutions throughout the process. The protein purification does not require sterile conditions.

After dissolution in a protein-compatible medium, the proteins obtained by salting-out precipitation can be directly subjected to purification and separation in the manner described below. The 90% salt-saturated supernatant of the last precipitation step is concentrated. For instance, by dehydration dialysis or ultrafiltration, all compounds having a molecular weight higher than about 300 to 500 daltons are obtained as a retentate fraction. They can also be further processed for purification of salt-soluble chemorecruitins.

The protein fractions obtained in the step described above contain the mediator proteins of the invention in admixture with numerous foreign proteins, e.g. other secreted proteins, in part serum albumins and in part CON. These foreign proteins form the major part of the constituents of this mixture. The mediator proteins must be further purified by a sequence of further purification steps. Foreign proteins must be removed to avoid interference with the molecular-biological specifity of mediator proteins. In addition, mediator proteins themselves form a class of protein compounds which must be separated into individual, specifically acting structures.

In general, purification processes for proteins and other natural substances comprise sequences of combined separation techniques. Subtle differences in molecular size, charge, form, structure stability and nature of the molecular surfaces between the desired natural substance and the accompanying inactive foreign materials are used in such purification steps for their separation. Accordingly, a large number of combinations of various modifications of preparation techniques can be devised for the purification of a protein. The nature and the conditions of the preparation steps used, but also their sequential combination, are of paramount significance for operational properties, technical practicability, possibility of optional automatization and for the economical performance of a purification process and also for the yield and molecular quality of a natural product investigated. Particular attention has to be given to the optimum form of separation steps and on their ingenious combination into a purification sequence within the framework of structural and functional stability and other molecular parameters of the substance under investigation. This implies that the use of identical or similar separation principles (molecular sieve filtration, dialysis, ion exchange adsorption, etc.)—however in a different combination—can be of specific and paramount importance for the practice and economical performance of the purification process as well as for the yield and quality of the product obtained. In some cases, the use or omission of a single technique (e.g. hydroxyapaptite chromatography, zone precipitation chromatography, etc.) at a certain point in the purification sequence or within a partial sequence, is of decisive significance for the yield and quality of the desired natural product as well as for the practice and economical performance of the purification process. These general relationships and basic principles inherent to the purification processes of natural products are clearly illustrated e.g. by some well known facts. Thus, within an economically and technically operable process for the purification of a natural product, initial dialysis, ultrafiltration or lyophilization steps are not recommended prior to reduction of original volumes of crude starting extracts by a factor of at least 500 to 1000 through other techniques.

For the purification of the individual protein fractions, a plurality of purification steps so far known in biochemistry can be used. Examples of such purification steps are: Preparative and analytical molecular sieve chromatography, anion and cation exchange chromatography and batch adsorption techniques, chromatography on hydroxyapatite, zone precipitation chromatography and recycling or cascade molecular sieve filtration.

It is possible to remove a considerable amount of accompanying foreign proteins from mediator proteins by only one performance of these purification methods. However, proteins contained in the fractions tend to adhere together very strongly. Therefore, for example, in spite of different molecular weights of proteins, using molecular sieve filtration, no complete (ideal) separation of protein polyelectrolytes according to their exact molecular weight is obtained immediately. Hence it is necessary to perform at least two of the mentioned separation processes in sequence. A particularly preferred embodiment of the process in accordance with the invention uses three of the mentioned purification steps in sequence for the purification of mediator protein activity from the protein fractions.

All combinations of the mentioned separation steps constitute objects of the invention. It is evident, that certain sequences of separation steps are of less advantage than other combinations. Thus, for example, it is imperative to perform a preparative molecular sieve filtration before an analytical molcular sieve filtration: In reverse order of performance, difficulties in handling, economic efficiency and yield are obvious.

Molecular sieve filtration achieves separation of proteins according to their molecular weights. Since the bulk of the foreign proteins have molecular weights different from those of mediator proteins they can be separated off in this manner. A hydrophilic water-swelling molecular sieve as matrix is used for separation of the proteins by molecular weight. Examples of suitable molecular sieve matrices are dextrans cross-linked with epichlorohydrin (Sephadex), agaroses cross-linked with acrylamides (Ultrogels), and three-dimensionally cross-linked acrylamides (Biogels). The exclusion limits of the matrices used are higher than the separation limits.

If several separation steps are used, the molecular sieve filtration is preferably carried out as one of the first separation steps. Depending on the length-to-diameter ratio of the column used and the particle diameter of the gel matrix, molecular sieve filtration is termed "preparative" or "analytical". A molecular sieve filtration is "preparative" when the chromatography is performed on columns with a length-to-diameter ratio of up to 10:1 and a charge of the column of up to $\frac{1}{3}$ of its capacity in terms of the total separation volume of the matrix. "Analytical" molecular sieve filtration means a length-to-diameter ratio larger than 10:1, and preferably about 50:1, and a maximum charge of the column of up to 3% of its capacity.

In preparative molecular sieve chromatography, gel matrices with the largest particle size are used for maximum flow-through rates of mostly viscous protein solutions applied at reasonably low pressures. In analytical molecular sieve filtration the particle size ranges of the gel matrix are selected as small as possible, to obtain a maximum number of theoretical plates, a flow rate of the mobile phase in the range of 2 to 4 cm/h combined with a pressure which is limited to technical and safety aspects. These parameters are dependent on the structure of the gel matrix and may vary from gel to gel.

If several preparative molecular sieve filtrations are performed in sequence, graduated separation limits can be selected. This can be followed by an analytical molecular sieve filtration with correspondingly graduated separation limits. The exclusion limit of the gel used must in all cases be higher than about 10,000 daltons to allow a volume distribution of mediator proteins between the stationary gel matrix phase and the mobile aqueous buffer phase.

The "exclusion limit" is a hydrodynamic parameter of a dissolved particle, which corresponds to the pore size of the gel matrix. Particles with a greater hydrodynamic parameter cannot penetrate the gel matrix (volume distribution coefficient $K_D=0$). The "separation limit" refers to a hydrodynamic parameter which has been chosen for the separation of dissolved particles from others and which has a value of between the volume distribution coefficient $K_D=0$ and $K_D=1$.

For molecular sieve filtration, the proteins are applied to the molecular sieve after dissolution in a protein-compatible liquid. A special example of a suitable solvent is 0.003 mol/l sodium-potassium phosphate solution containing 0.3 mol/l NaCl and 0.001 mol/l cysteine and having a pH of 7.4. After filtration, the mediator protein-containing fractions are concentrated in the manner described below and optionally subjected to a further purification step.

Examples of suitable anion exchangers are dextran matrices cross-linked with epichlorohydrin (Sephadex) or cellulose matrices carrying functional groups with anion exchanger capacity. These exchangers can be regenerated for repeated further use. It is preferable to use a weak anion exchanger in the $Cl^-$ form such as DEAE-Sephadex A-50, pre-swollen and equilibrated in a buffer. Swelling and equilibration is preferably carried out at a pH of 8 to 10. A special example of such a buffer solution is 0.01 mol/l tris-HCl containing 0.04 mol/l NaCl and 0.001 mol/l cysteine and having a pH value of 8.0.

The anion exchanger is added to the protein fraction in an amount sufficient for complete adsorption of the mediator proteins and of the other positively adsorbing accompanying proteins. Two volume parts of swollen anion exchanger per volume of concentrated protein solution are normally sufficient. The reaction can be carried out either as chromatographic process or as an easy and fast batch adsorption technique. In the latter case, the supernatant liquid containing negatively adsorbed proteins is separated from the anion exchanger which is charged with the positively adsorbed mediator proteins or other proteins, e.g. by filtration in a chromatographic column, by decantation or centrifugation. The charged anion exchanger is freed from adhering negatively adsorbing compounds by washing with water or a salt solution having a maximum ionic strength equivalent to 0.04 mol/l NaCl, preferably at a pH of 8 to 10.

The maximum preferred temperature is about 15° C. A special example of salt solution suitable for the washing-out process is the tris-HCl buffer of pH 8.0.

The anion exchanger on which the mediator proteins and other proteins are adsorbed and which is freed from the negatively adsorbed compounds is eluted with a protein-compatible aqueous salt solution having an ionic strength higher than 0.04 mol/l NaCl and a pH of between 4.0 and 10.0. A salt solution of high ionic strength and a pH of between 5.0 and 7.0 is preferably used. A special example of such a salt solution is a 2.0 mol/l NaCl solution buffered to a pH of 6.5 with 0.01 mol/l piperazine-HCl and containing 0.001 mol/l cysteine.

If the anion exchange reaction is carried out as a chromatographic process, elution of the mediator proteins and other positively adsorbed proteins can also be done by a linear NaCl concentration gradient.

Examples of cation exchange matrices suitable for the purification of the protein fraction are dextrans cross-linked with epichlorohydrin (Sephadex) or cellulose matrices carrying functional groups with cation exchange capacity. These can be readily regenerated after use and employed again. It is preferable to use a weakly acidic cation exchanger such as CM-Sephadex C-50 having $Na^+$ as mobile counter-ion, and to perform the exchange reaction at a pH between 4 and 6. To facilitate the charge process and to approach more ideal equilibria conditions prior to treatment with the cation exchanger the protein fractions should be diluted with a protein-compatible salt solution having a maximum ionic strength equivalent to 0.04 mol/l NaCl. This salt solution can be used at the same time to adjust the pH. A special example of a salt solution for this purpose is a 0.001 mol/l potassium phosphate-acetate buffer containing 0.04 mol/l NaCl and 0.001 mol/l cysteine and having a pH of 4 to 6. This cation-exchange reaction may be performed as a chromatographic process, or technically easier, as a batch process.

The swollen cation exchanger is added to the protein fraction in a quantity sufficient to adsorb it. As a rule, about 2 volume parts of swollen ion exchanger per volume part of protein solution is sufficient for this purpose. The supernatant is then separated from the cation exchanger charged with proteins, for example by decantation or centrifugation. The charged cation exchanger is freed from adhering, negatively adsorbed compounds by washing with water or a salt solution, having a maximum ionic strength equivalent to 0.04 mol/l NaCl. Preferably a pH of about 4 to 6 and a maximum temperature of about 15° C. is used. A special example of a salt solution suitable for the washing out process is the mentioned potassium phosphate-acetate buffer having a pH of 5.0.

The washed protein-charged cation exchanger is now eluted with a protein-compatible aqueous salt solution. A salt solution of high ionic strength with a pH of about 4 to 10 is preferably used for this purpose. Special examples of such salt solutions are aqueous 0.5 mol/l potassium phosphate with a pH of 6.5 to 7.5 or a 2 to 5 mol/l NaCl with the same pH.

For chromatography on hydroxyapatite, salts, e.g. ammonium sulfate and especially phosphates, possibly present from preceding steps are removed from the protein solution, preferably by dialysis or ultrafiltration at membranes with an exclusion limit of 500 daltons prior to the application of the proteins to hydroxyapatite. Apart fom viscosity increase by accompanying salts, however, only the phosphate concentration of the protein solution is critical for the chromatography on hydroxyapatite. The mediator proteins are eluted by a potassium phosphate concentration gradient which is preferably linear. The mediator protein containing fractions are collected and then concentrated in the manner described below.

The use of hydroxyapatite is of essential significance for the structure-conserving isolation of pure mediator proteins. However, in general, for technical and economic reasons, considerable difficulties arise from chromatography of larger volumes of protein solutions on hydroxyapatite columns. On the one hand, larger protein amounts contribute to the strong tendency of hydroxyapatite to clog, thus becoming unusable as stationary matrix in chromatography. On the other hand, hydroxyapatite is very expensive. Its use on larger scales is not economical. For these reasons, in the process of the invention, the separation of a large part of the accompanying foreign proteins by appropriate biotechnical purification steps from the mediator protein-containing protein fractions is preferred for considerably reducing the volume of the protein solution prior to its chromatography on hydroxyapatite.

In the zone precipitation chromatography (cf. J. Porath, Nature, vol. 196 (1962); p. 47–48), residual protein contaminations in the mediator proteins are separated by salting-out fractionation of the proteins by means and along a salt concentration gradient. The basic principle of separation of proteins in zone precipitation chromatography are different, structure-related, reversible solubility characteristics of proteins. They belong to the most sensitive molecular separation criteria and are often used for demonstration of molecular homogeneity of a protein. Two variants of this technique for development of the chromatogram are known: Fractional precipitation zone chromatography and fractional elution zone chromatography. Both types of techniques may have selective advantages in specific cases as described for fractional precipitation and fractional elution methods in protein separation. Temperature and pH, column characteristics can all be varied within relatively wide limits.

The temperature for zone precipitation chromatography can be between 0° and 40° C. Preferably, a temperature range from about 0° to 10° C. is used, especially from about 4° to 6° C. The pH can be between 4 and 10; preferably, a pH range of 6 to 8 is used, especially a pH of about 7. The length-to-diameter ratio of the column used should be greater than about 10:1. A ratio of 30 to 100:1 and especially of about 50:1 is preferred. All protein-compatible salts having salting-out properties for proteins are suitable. Examples of such salts are sodium-potassium phosphate, ammonium sulfate, and sodium sulfate. Ammonium sulfate is preferred.

The salt concentration gradient can have any desired shape provided that salting-out criteria of proteins achieve protein separation. Linear concentration gradients are preferred, especially as ascendent linear concentration gradient from 25 to 100% ammonium sulfate saturation. The maximum column charge is about 5% and preferably about 1% of total column volume.

The recycling or cascade molecular sieve filtration can be performed under the conditions described above for the analytical molecular sieve filtration. The same molecular sieves and the same column conditions can be used. Sephadex G 50 as stationary matrix is preferred in a column of a length-to-diameter ratio of at least about 50:1 and a maximum charge of about 3% of the column volume. The solvents used in the analytical molecular sieve filtration are also preferred as solvents for the elution in this method.

In recycling molecular sieve filtration, the distribution equilibria are disturbed continuously and the eluate is recycled onto the same column with fixed separation limits. In this way, the separation length of the migrating protein distribution bands are differentially extended. Alternatively, in cascade molecular sieve filtration, distribution equilibria are disturbed by continuous transfer of the eluate into a new second column with the same or similar, defined parameters at fixed separation limits.

Between the above-described purification steps, and if necessary at any stage for special purposes, protein solutions can be separated and freed from unwanted salts and water as well as concomitantly concentrated. The concentration (separation of a major portion of aqueous salt solution of the protein) can be achieved in different ways. Dehydration dialysis or ultrafiltration against protein-compatible liquid, preferably a sodium potassium phosphate buffer, are such methods. Dehydration dialysis is carried out preferably against polyethylene glycol (molecular weight 20,000 daltons) at membranes with exclusion limites of preferably 500 daltons. Ultrafiltration is preferably achieved at membranes with an exclusion limit of about 500 daltons. Small amounts of protein precipitates formed are removed by intermediary centrifugation to result in a clear protein solution. A desalting molecular sieve filtration on matrices with appropriate separation and exclusion limits can as well be used for this purpose, e.g. on Sephadex G 10, G 15 or G 20 as matrices. Furthermore, by selecting an appropriate mobile phase in the usual way, a usual molecular sieve filtration step can also be used concomitantly for this purpose.

To prevent sulfhydryl group oxidation, about 0.001 mol/l of cysteine is preferably added to protein solutions throughout.

In the molecular sieve filtration purification steps about 0.4 mol/l ammonium sulfate is preferably added to the protein solution. In contrast to higher concentrations of this salt, at this concentration ammonium sulfate exerts a strong salting-in effect on proteins. Thus, proteins are better kept in solution during the molecular sieve filtration. Moreover, ammonium sulfate prevents growth of microorganisms and inhibits certain enzymes. Hence, it contributes to stabilization of the mediator protein structure which is important when chromatography is performed at higher temperature (above about 20° C.) and under nonsterile conditions.

Mediator proteins which can be salted out are preferably completely precipitated alone or together with accompanying proteins by adding ammonium sulfate up to a concentration of about 3.25 to 3.7 mol/l (80 to 90% saturation). For this purpose 630 g/l ammonium sulfate are added (about 90% saturation). The pH value is preferably kept between 4 and 9 and the temperature up to 40° C., preferably between 0° and 8° C. The mediator protein-containing protein precipitate is separated from the protein-free supernatant solution by filtration, decantation or centrifugation. Unless otherwise stated, centrifugation is preferably carried out at least at 10,000×g for a minimum of 45 min, and preferably for 1 h, in a one-step process. Or it can be carried out in two stages, at lower forces in the first stage for removal of the bulk of precipitated proteins; and then, for the supernatant of the first stage containing residual fine protein particles at higher forces, e.g. 20,000 to 50,000×g, by flow-through centrifugation.

The temperature and pH conditions during performance of the purification steps are not particularly critical. If the native conformation of the protein is to be preserved, an optimum temperature range is about 0° to 8° C., and preferably about 0° to 4° C. Moreover, the separation and purification steps must be carried out under essentially physiological pH and salt conditions. An essential advantage of the process of the invention consists in that these conditions are for the first time easy to adhere to.

The mediator proteins obtained can be stored in a buffered physiological saline, e.g. in 0.0015 mol/l sodium-potassium phosphate solution containing 0.15 mol/l (0.9 w/v%) NaCl, 0.001 mol/l cysteine and having a pH of 7.4. After usual sterilization by filtration (pore diameter 0.2 μm), the protein preparation remains native and biologically active at room temperature for at least 200 h or frozen at −25° C. for at least 5 years. This stability of the protein can be considered, among others, to be one of the criteria of molecular homogeneity. Mediator protein solutions are safely stored at temperatures of between −20° and +50° C. in the presence of 2.0 to 3.6 mol/l ammonium sulfate (50 to 90% saturation). At this high osmotic pressure mediator protein solutions are protected against infection and degradation by microorganisms and bacterial growth. For their physiological, therapeutical and any other use, the mediator proteins are again freed from salts by dialysis or ultrafiltration against an appropriate saline as described above.

The invention will now be given in detail by examples describing the isolation of the mediator protein preparation starting from leukocytes of porcine blood. However, the invention is not restricted to this embodiment. Leukocytes and inflamed tissues of other mammalians can be used too.

EXAMPLE A

Preparation of Chemokinesins and Chemotaxins From Supernanatants of Cultures of a Mixed Population of Viable Leukocytes The production of chemokinesins and chemotaxins in a culture solution of a mixed population of leukocytes and the separation of lymphocytomonoapokinesin (LMAK), monocyto-granuloapokinesin (MGAK), monocyto-granuloproskinesin (MGPK), lymphocytomonoproskinesin (LMPK), monocyto-granulotaxin (MGT), granulocyto-monotaxin (GMT) and monocyto-eosinotaxin (MET) from the other components of the culture supernatant are described. All process steps are carried out at 0° to 8° C. in the presence of 0.001 mol/l cysteine, unless otherwise specified. The centrifugation is carried out in the manner described, either as a one or two step procedure (as flow-through centrifugation).

A. 1. Preparation and culture of a mixed population of viable leukocytes 50 kg (about $10^{14}$) leukocytes are isolated as mixed cell population of physiological composition from 10,000 l of porcine blood and cultured in 20 batches of 2.5 kg (about $5\times10^{12}$ cells) under sterile conditions. The medium indicated in table VIII is used as culture solution. 50 l of culture medium are used per batch. Culturing is performed in glass vessels (Duran 50 or Pyrex glass). Initially, the cell density is about $10^8$ cells/ml. The culture is maintained at 37° C. in an atmosphere of 1 v/v % $CO_2$ over 40 hours. During this period, the cell suspension is slowly stirred (to r.p.m.) and flooded with sterile, water-washed and heat-decontaminated air bubbles (<1 mm). The heat-decontamination of air is performed at about 500° C. by flowing through a silica tube. In addition to the partial oxygen pressue, the pH value (7.1) and the D-glucose level are measured and maintained constant. During culturing, the cells are induced to mitosis by the polyvalent mitogen content (CON) of the culture medium. The number, differential and morphological viability (dye exclusion test) of the cells are continuously determined by usual methods of hematology and cell culture techniques. The functional viability of cells is measured by their motility and their ability to respond to chemokinetic and chemotactic proteins. Mitoses are determined by chromosome count. The morphological viability of the cells after their biotechnical culturing is 95%. The entire loss in cells (mainly granulocytes) during culturing is at most 20% which is normal for primary cell cultures. The culture is terminated by separating the cells from the supernatant solution by centrifugation for 10 minutes at 400×g and 10° C. The cells are washed twice in a salt solution containing 0.15 mol/l NaCl, 0.0015 mol/l sodium potassium phosphate and having the pH-value 7.1. They can be used for another purpose.

The culture supernatant solution is then centrifuged again for 1 hour at 10,000×g and at 4° C. to remove suspended particles. The resultant clear supernatant culture solution which has a total volume of 1000 liters and contains about 1,400 g protein as well as other macromolecules and salts is directly subjected to salting-out fractionation with ammonium sulfate (A2). Unless otherwise stated, all further steps are carried out at 0°–4° C.

A2. First purification step (salting-out fractionation): Preparation of crude protein concentrate fractions 0.5 mol/l sodium-potassium phosphate buffer solution with a pH value of 6.7 is added to the supernatant culture solution (A 1) up to a final concentration of 0.1 mol/l. Furthermore, solid L-cysteine is added up to a concentration of 0.001 mol/l.

This buffered supernatant culture solution is then adjusted to 35% saturation of ammonium sulfate by addition of 199 g of ammonium sulfate/l solution. During the addition, the pH-value of the protein solution is continuously controlled and maintained at 6.7 by the addition of 2 n ammonia. Part of the proteins is precipitated from the solution. The protein precipitate formed is separated from the supernatant containing salt-soluble proteins by centrifugation for 1 hour at 10,000×g. The precipitated crude protein fraction I is obtained as ammonium sulfate-containing protein sludge which contains about 100 g protein. This crude protein concentrate fraction I may separately be processed for its constituents according to the procedure described below for the crude protein concentrate fraction III.

Then the 35% salt-saturated supernatant culture solution is adjusted to 45% saturation of ammonium sulfate by adding 60 g of ammonium sulfate/l solution. The pH value of the protein solution is continuously controlled and maintained constant at 6.7 by 2 n ammonia. Another protion of proteins is pecipitated from the solution. The protein precipitate is separated from the supernatant containing salt-soluble proteins by centrifugation for 1 hour at 10,000×g. The precipitated crude protein concentrate fraction II is obtained as ammonium sulfate-containing protein sludge, the protein content of which is about 60 g. This crude protein concentrate fraction II may be processed separately for its constituents, according to the procedure described below for the crude protein concentrate fraction III.

The 45% salt-saturated supernatant culture solution is then adjusted to 90% saturation of ammonium sulfate by adding 323 g of ammonium sulfate/l of solution. The pH-value of the protein solution is again continuously controlled and maintained constant at 6.7 by 2 n ammonia. Another portion of the proteins is precipitated from the solution. The protein precipitate is separated from the supernatant containing salt-soluble proteins by centrifugation for 1 hour at 10,000×g. The precipitated crude protein concentrate fraction III is obtained as ammonium sulfate-containing protein sludge the protein content of which is approximately 1,080 g. This fraction also contains the bulk of the serum albumin as component of the culture medium. This crude protein concentrate fraction III contains the mediator proteins of the invention and is processed according to the procedure described below. The 90% salt saturated supernatant fraction IV of the crude fraction III contains 160 g of salt-soluble proteins and other macro molecules (>500 daltons). It may also be processed for its constituents.

A.3. Fine purification of mediator proteins in the crude protein concentrate fraction III A.3.1. Anion exchange chromatography The crude protein concentrate fraction III obtained above (A 2) is dissolved in a minimum volume of buffer solution B (0.01 mol/l of tris-HCl solution containing 0.04 mol/l NaCl and 0.001 mol/l cysteine and having a pH value of 8.0). The resultant slightly turbid solution (20 l) is clarified by centrifugation and then freed of salts by dialysis at a membrane with the exclusion limit of 500 dalton against buffer solution B until no sulfate ions are detectable. The clear solution obtained is then applied to a column of a swollen regenerated anion exchanger ($Cl^-$ as mobile exchangeable ion). It has a dextran matrix cross-linked with epichlorohydrin (DEAE-Sephadex A 50) which is equilibrated in the above-mentioned buffer system B.

The column has four times the volume of the protein solution and a length-to-diameter ratio of 10:1. The gel column is then washed with the above-mentioned adsorption buffer solution B until the extinction of the filtrate at 280 nm is ≦1.0.

In this purification step, chemokinesins are separated from chemotaxins, because the former are adsorbed whereas the latter flow through.

For elution of the chemokinesins and the adsorbed proteins, the charged ion exchanger gel is eluted with a NaCl-concentration gradient during 2 days. The gradient is linearly ascending from 0.04 to 2.0 mol/l NaCl, whereas the pH value, the tris/HCl and the cysteine concentrations are maintained constant. The same shape of gradient is then used for lowering the pH from 8 to 6.5 for further elution of the compounds. It is made up by 0.01 mol/l piperacine-HCl-buffer containing 2.0 mol/l NaCl and 0.001 mol/l cysteine and having the pH 6.5.

The chemokinesin or chemotaxin-containing fractions are collected separately. They are separately processed in further purification steps described below (A.3.2–A.3.6).

A.3.2. Preparative molecular sieve filtration

After concentration of the proteins in the fractions (A.3.1) by salting-out precipitation with ammonium sulfate, the protein precipitate containing either chemokinesins or chemotaxins is dissolved in a minimum volume of buffer solution C (0.003 mol/l sodium-potassium phosphate containing 0.3 mol/l NaCl and 0.001 mol/l cysteine and having a pH value of 7.4). After removal of a small amount of insoluble compounds by centrifugation, the solution is applied to a column of a molecular sieve matrix of agarose cross-linked with acrylamide (Ultrogel AcA 34, particle size 60 to 160 μm) for preparative molecular sieve filtration. The column has 10 times the volume of the protein solution and a length-to-diameter ratio of 20:1. The column is then eluted with an upward flow (3 cm/h) of the mentioned buffer solution C. For chemokinesins, the fraction with the separation limits of 25,000 and 6,000 dalton and for chemotaxins, the fraction with the separation limits of 20,000 and 3,000 dalton are collected. For the concentration of the proteins, the fractions are lyophilized and ultrafiltrated at a membrane with the exclusion limit of 500 dalton or are adjusted to an ammonium sulfate concentration of 3.7 mol/l. In this case, the protein precipitates are separated from the supernatant by centrifugation and further processed as described below (A.3.3)

A.3.3 Cation exchange chromatography

The resultant chemokinesins or chemotaxins-containing protein precipitates (A 3.2) are dissolved in 1.5 volume parts of buffer solution D (0.01 mol/l sodium-potassium phosphate, 0.04 mol/l NaCl, 0.001 mol/l cysteine, pH 6.0). The solutions are centrifuged at 10,000×g for 1 hour for removal of a small amount of insoluble material.

The clear solution is dialyzed against the buffer solution D at a membrane with the exlusion limit of 500 dalton until no sulfate ions are detectable. The clear solution obtained is then applied to a column of swollen, regenerated cation exchanger based on a dextran matrix cross-linked with epichlorohydrin (CM-Sephadex C 50). The exchanger is equilibrated in the above-mentioned buffer system D ($Na^+$ as mobile exchangeable ion).

The column has four times the volume of the protein solution and a length-to-diameter ratio of 10:1. The gel column is then washed with the above-mentioned adsorption buffer solution D, until the extinction of the filtrate at 280 nm is ≦1.0.

For elution of the mediator proteins and the adsorbed proteins, the charged ion exchange gel is eluted with an NaCl-concentration gradient during 2 days. The gradient is linearly ascending from 0.04 to 2.0 mol/l NaCl whereas the pH-value and the phosphate and cysteine concentrations are maintained constant. For further elution, the same shape of gradient is then used for increasing the phosphate concentration from 0.01 to 0.5 mol/l at a pH of 8.0, whereas the NaCl (2 mol/l) and cysteine concentrations are kept constant.

The chemokinesins or chemotaxins-containing fractions are collected and concentrated in the usual manner and further processed as described below (A.3.4).

A.3.4 Chromatography on hydroxyapatite

The chemokinesins or chemotaxins-containing protein precipitates (A.3.3) are dissolved in a minimum volume of 0.0001 mol/l sodium-potassium phosphate buffer solution E containing 0.001 mol/l cysteine and having a pH of 7.20. The solutions are then desalted with this buffer by molecular sieve filtration, ultrafiltration or dialysis (exclusion limit 500 dalton), until no sulfate is detectable in the dialysis buffer. Thereafter, a small portion of insoluble material is removed by centrifugation at 10,000×g for 1 hour.

The clear chemokinesins or chemotaxins-containing protein solutions obtained are separately applied to a column of hydroxyapatite. The length-to-diameter ratio of the column is 10:1 and it has four times the volume of the protein volume to be applied. The column has been equilibrated with the mentioned buffer E used in an amount five times the column volume (flow 3 cm/h).

The negatively adsorbed proteins are washed out with the buffer solution E used for equilibrating the column. The elution of the mediator protein-containing fractions is carried out with a phosphate concentration gradient for 4 days. The gradient is linearly ascending from 0.0001 mol/l to 0.5 mol/l sodium-potassium phosphate having a constant pH value of 7.4 and constant cysteine concentration.

The different mediator proteins are separated in this step. LMAK is eluted at an average phosphate concentration of about 0.04 mol/l, MGAK at about 0.001 mol/l, MGPK at about 0.005 mol/l, LMPK at about 0.08 mol/l. In the chromatogram of the chemotaxins MGT appears at an average phosphate concentration of about 0.004 mol/l, MET at about 0.05 mol/l and GMT at about 0.2 mol/l. The elution gradient is measured and controlled by means of conductivity. The mediator protein-containing fractions are concentrated in the usual manner and further processed as described below (A.3.5).

A.3.5. Zone precipitation chromatography

The mediator protein-containing fractions (A.3.4) are dissolved in 0.1 mol/l sodium-potassium phosphate solution F containing 0.1 mol/l NaCl, 0.001 mol/l cysteine and 1 mol/l ammonium sulfate and having a pH value of 7.4. The resultant solution is applied at a temperature of 4° C. to a column of swollen molecular sieve matrix of dextran cross-linked with epichlorhydrin (Sephadex G-25). In the matrix, an ascendent, linear ammonium sulfate concentration gradient is established with the mobile buffer phase from 1.0 to 4.0 mol/l ammonium sulfate (25 to 100% saturation). The slope of the gradient is +2% of the ammonium sulfate saturation/cm of column height (0.08 mol/l $(NH_4)_2SO_4$/cm). The range of the gradient extends over approximately half the length of the column.

The length-to-diameter ratio of the column is 50:1, the column volume is 100 times higher than the protein solution volume to be applied. The flow rate is 2 cm/h.

The elution is carried out with the above-mentioned sodium-potassium phosphate solution F containing 1 mol/l of ammonium sulfate. The mediator protein-containing fractions which are eluted at 65% (LMAK), 77% (MGAK), 72% (MGPK), 62% (LMPK), 70% (MGT), 57% (GMT) and 80% (MET) ammonium sulfate saturation, respectively, are collected. The proteins are concentrated in the usual manner and further processed as described below (A.3.6).

A.3.6. Analytical recycling molecular sieve filtration

The mediator protein-containing fractions (A.3.5) are dissolved in buffer C (0.003 mol/l sodium-potassium phosphate containing 0.3 mol/l NaCl and 0.001 mol/l casteine and having a pH value of 7.4). Removal of a small portion of insoluble substances is achieved by centrifugation for 30 minutes at 48,000×g.

The resultant clear solution is then subjected to analytical recycling molecular sieve chromatography. For this purpose, the solution is applied at a temperature of 4° C. to a column of Ultrogel AcA 44 having a particle size of 60 to 140 μm. The column has 50 times the volume of the protein solution and a length-to-diameter ratio of 50:1. The elution is carried out with the mentioned buffer C. The eluates are recycled three times at separation limits of either 17,000 dalton (LMAK), 12,000 dalton (MGAK), 19,000 dalton (MGPK), 25,000 dalton (LMPK), 13,000 dalton (MGT), 20,000 dalton (GMT), or 8,000 dalton (MET). After usual protein concentration, approximately 3 mg of LMAK, 5 mg of MGAK, 5 mg of MGPK, 4 mg of LMPK, 6 mg of MGT, 9 mg of GMT and 5 mg of MET are obtained. The chemokinesins and chemotaxins have a molecular homogeneity of >95%, as indicated by conventional methods.

In the following flow sheet the above-described process for preparing and isolating the chemokinesins and chemotaxins of the invention is schematically represented.

FLOW SHEET FOR BIOTECHNICAL PURIFICATION OF LEUKOCYTE-DERIVED CHEMOKINESINS AND CHEMOTAXINS

| STEP | |
|---|---|
| | STERILE CELL CULTURE |
| 1st | CELL CULTURE SUPERNATANT |
| 2nd | SALTING-OUT PRECIPITATION WITH AMMONIUM SULFATE |
| | 90% SATURATION FRACTION |
| 3rd | ANION EXCHANGE CHROMATOGRAPHY |
| 4th | MOLECULAR SIEVE FILTRATION |
| 5th | CATION EXCHANGE CHROMATOGRAPHY |
| 6th | HYDROXYAPATITE CHROMATOGRAPHY |
| 7th | ZONE PRECIPITATION CHROMATOGHRAPHY |
| 8th | CASCADE MOLECULAR SIEVE FILTRATION |

LYMPHOCYTO-MONOAPOKINESIN
MONOCYTO-GRANULOAPOKINESIN
MONOCYTO-GRANULOPROSKINESIN
LYMPHOCYTO-MONOPROSKINESIN
MONOCYTO-GRANULOTAXIN
GRANULOCYTO-MONOTAXIN
MONOCYTO-EOSINOTAXIN

EXAMPLE B

Preparation of Mediator Proteins from Supernatants of Cultures of Viable Lymphocytes 15 kg (about $3\times10^{13}$) lymphocytes obtained from porcine blood are cultured under the conditions described in example A. During culture, the polyvalent mitogen (CON) in the medium induces the mitosis of the cells.

The chemokinesins LMAK and LMPK secreted to the culture solution are isolated according to the procedure described in example A. They are thereby obtained in a highly purified state. The yields obtained are comparable to those of example A.

EXAMPLE C

Preparation of Mediator Proteins from Supernatants of Cultures of Viable Monocytes Example B is repeated with a culture of 3,5 kg (about $7\times10^{12}$) monocytes. The chemokinesins and chemotaxins of the monocytes are obtained in yields as in example A.

EXAMPLE D

Preparation of Mediator Proteins from Inflamed Tissue Sites

The preparation and isolation of chemokinesins and chemotaxins from inflamed tissue are described. 500 g of infarcted, inflamed canine heart muscle tissue are used. The heart muscle tissue is ground at 0°–4° C. 0.05 mol/l sodium potassium phosphate buffer solution containing 0.001 mol/l cysteine and having a pH of 6.8 is added in a quantity three times the amount of the tissue. The resultant suspension is homogenized in a homogenizer (ultraturax). Thereafter, the supernatant containing the soluble compounds of the inflamed tissue is separated from the insoluble constituents by centriguation at 10,000×g and 4° C. The resultant supernatant solution is then centrifuged for 3 hours at 100,000×g. The clear supernatant solution obtained is siphoned off from the flotating lipid layer.

The mediator protein-containing clear supernatant protein solution is then subjected to fractional salting-out precipitation with ammonium sulfate according to example A. The resultant protein fraction III is then processed as described in example A. The yields, as compared to example A, are about 50% with the proteins from monocytes and granulocytes and only about 10% with the proteins from lymphocytes.

EXAMPLE E

Preparation of Mediator Proteins from Leukocyte Homogenates

Leukocytes are prepared from blood according to example A. A homogenate of 500 g of leukocytes is prepared as shown in example D for muscle tissue. The isolation of the protein mediators contained in the leukocytes is performed according to example A. The leukocytes cultured without stimulation contain only relatively small (about 1%) amounts of monocyte- and lymphocyte-chemokinesins and -chemotaxins, whereas the GMT is contained in a yield of about 10% compared with example A.

What is claimed is:

1. Leukocyte derived chemokinesins and chemotaxins, characterized by the following properties:
   (a) biological activities in vivo and in vitro:
      selective reversible influence on the motility of leukocytes (chemokinesis) or selective chemical attraction of leukocytes (chemotaxis) in vitro;
   (b) physico-chemical properties:
      soluble in aqueous media including in 15% ethanol at a pH value of at least 4.0 to 10;
      insoluble in ammonium sulfate solution at 90% saturation (3.6 mol/l)
      electrophoretic migration in acrylaminde matrices at a pH of 7.40 is anodic.
      they adsorb reversibly in structure and biological activity on anion and cation exchangers, calcium phosphate gel and hydroxyapatite and can be subjected in native form to volume partition chromatography.

2. Chemokinesins according to claims 1, characterized in that they reversibly lower the motility (statistical cell locomotion) of the leukocytes (negative chemokinesis=apochemokinesis).

3. Chemokinesin (lymphocyto-monoapakinesin) according to claim 2, characterized in that it is obtainable from lymphocytes and possesses the following additional properties:
   (a) biological effects:
      specific reversible lowering of the motility of macrophages (monocytes) in vitro;
      effective threshold dose in vitro: −2 nmol/l;
   (b) physico-chemical properties:
      molecular weight of the native protein (primary structure): approximately 14,000 dalton;
      absorption spectrum (UV, visible and near IR-range) as given in FIG. 1;
      extinction coefficients according to the following Table I:

TABLE I

| Wave length, nm | $E_{1\ mg/ml,\ 1\ cm}$ ($H_2O$, 20° C.) + 6% |
|---|---|
| 248 (min) | 0.43 |
| 260 | 0.59 |
| 277 (max) | 0.86 |
| 280 | 0.84 |
| 290 | 0.47 |
| 400–1000 | 0 |
| $E_{280}/E_{260}$ | 1.42 |

4. Chemokinesin (monocyto-granuloapokinesin) according to claim 2, characterized in that it is obtainable from mononuclear leukocytes and possesses the following additional properties:
   (a) biological activities:
      specific reversible lowering of the motility of granulocytes in vitro;
      effective threshold dose in vitro; <1 nmol/l;
   (b) physico-chemical properties:
      molecular weight of the native protein (primary structure): approximately 9,000 dalton;
      no protein quaternary structure in the form of physically bound peptide subunits: each of the native proteins consists of only one peptide unit;
      constant temperature coefficient of solubility in ammonium sulfate solutions between −10° C. and +50° C.;
      absorption spectrum (UV, visible and near IR-range) according to FIG. 2;
      extinction coefficient according to the following Table II:

TABLE II

| Wave length, nm | $E_{1\ mg/ml,\ 1\ cm}$ ($H_2O$, 20° C.) + 6% |
|---|---|
| 249 (min) | 0.39 |
| 260 | 0.48 |
| 278 (max) | 0.71 |
| 280 | 0.70 |
| 290 | 0.48 |
| 400–1000 | 0 |
| $E_{280}/E_{260}$ | 1.45 |

5. Chemokinesins according to claims 1, characterized in that they reversibly increase the motility (statistical cell locomotion) of the leukocytes (positive chemokinesis=proschemokinesis).

Figure 3:
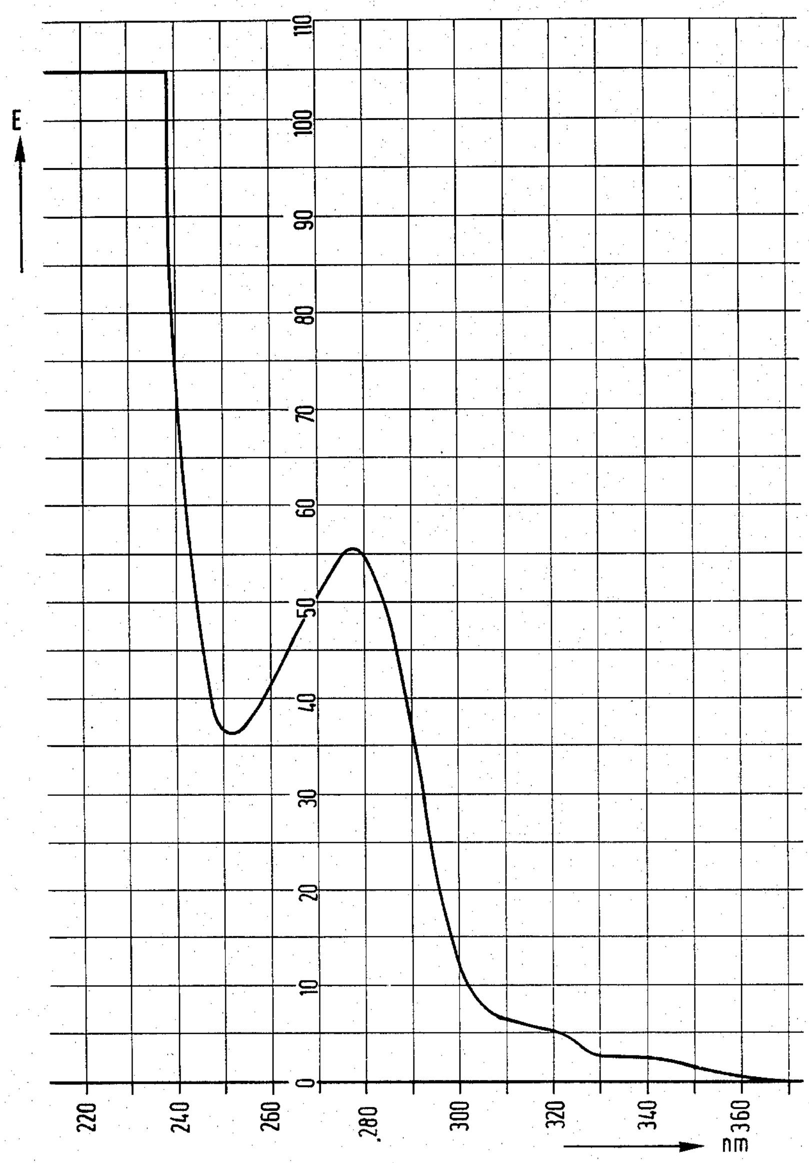

6. Chemokinesin (monocyto-granuloproskinesin) according to claim 5, characterized in that it is obtainable from mononuclear leukocytes and possesses the following additional properties:
   (a) biological activities:
      specific reversible increase of the motility of granulocytes in vitro;
      effective threshold dose in vitro: <2 nmol/l;
   (b) physico-chemical properties:

molecular weight of the native protein (primary structure): approximately 16,000 dalton;

absorption spectrum (UV, visible and near IR-range) as given in FIG. 3;

extinction coefficient according to the following Table III:

TABLE III

| Wave length, nm | $E_{1\ mg/ml,\ 1\ cm}$ ($H_2O$, 20° C.) + 6% |
|---|---|
| 251 (min) | 0.36 |
| 260 | 0.42 |
| 278 (max) | 0.56 |
| 280 | 0.54 |
| 290 | 0.35 |
| 400-1000 | 0 |
| $E_{280}/E_{260}$ | 1.29 |

Figure 4:
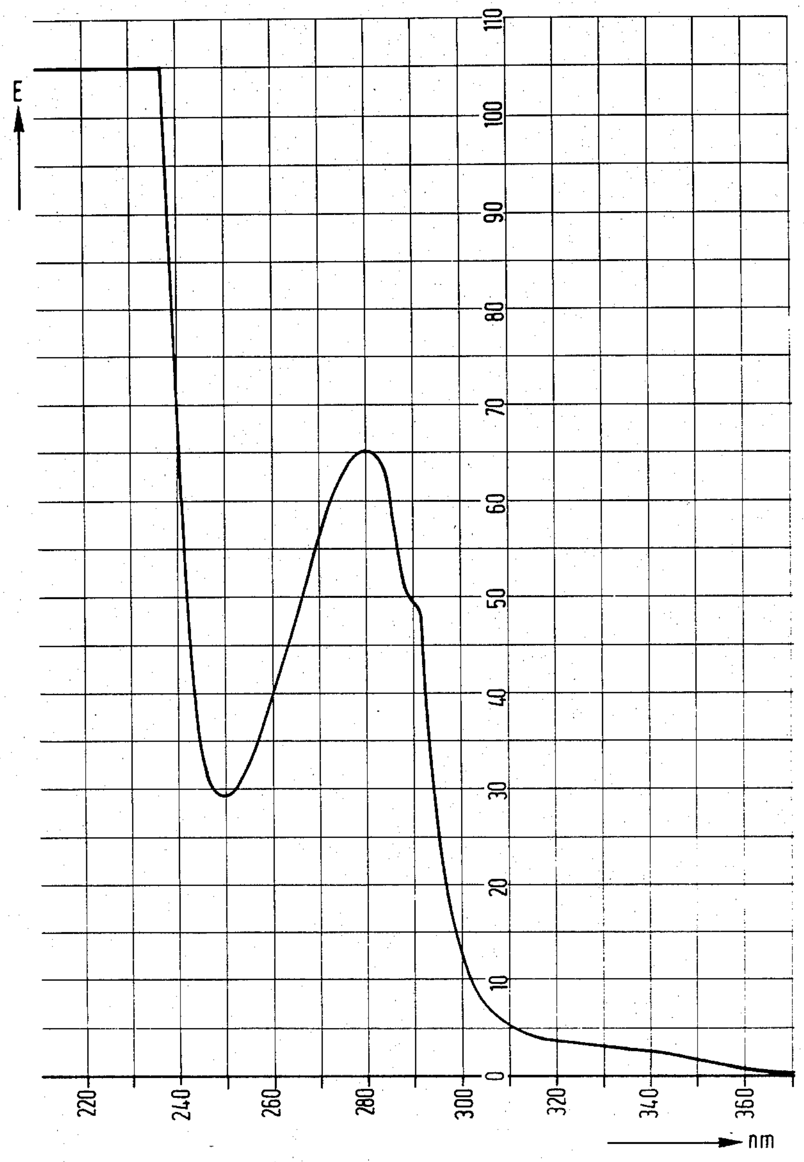

7. Chemokinesin (lymphocyto-monoproskinesin) according to claim 5, characterized in that it is obtainable from lymphocytes and possesses the following additional properties:

(a) biological activities:

specific increase of the motility of macrophages (monocytes) in vitro;

effective threshold dose in vitro: <10 nmol/l;

(b) physico-chemical properties:

molecular weight of the native protein (primary structure): approximately 22,000 dalton;

adsorption spectrum (UV, visible and near IR-range) as given in FIG. 4;

extinction coefficient according to the following Table IV:

TABLE IV

| Wave length, nm | $E_{1\ mg/ml,\ 1\ cm}$ ($H_2O$, 20° C.) + 6% |
|---|---|
| 249 (min) | 0.29 |
| 260 | 0.40 |
| 279 (max) | 0.65 |
| 280 | 0.65 |
| 290 | 0.49 |
| 400-1000 | 0 |
| $E_{280}/E_{260}$ | 1.62 |

8. Chemotaxins according to claims 1, characterized in that they chemically attract leukocytes and produce a directed cell migration along their concentration gradient (chemotaxis).

9. Chemotaxin (monocyto-granulotaxin) according to claim 8, characterized in that it is obtainable from mononuclear leukocytes and possesses the following additional properties:

(a) biological activities:

chemical attraction of neutrophilic granulocytes in vitro;

accumulation of neutrophilic leukocytes in situ with indirect cell-induced angiogenesis and inflammation reaction;

effective threshold dose in vitro: <0.5 nmol/l;

(b) physico-chemical properties:

molecular weight of the native protein (primary structure): approximately 11,000 dalton;

absorption spectrum (UV visible and near IR-range) as given in FIG. 5;

extinction coefficient according to the following Table V:

TABLE V

| Wave length, nm | $E_{1\ mg/ml,\ 1\ cm}$ ($H_2O$, 20° C.) + 6% |
|---|---|
| 253 (min) | 0.51 |
| 260 | 0.54 |

TABLE V-continued

| Wave length, nm | $E_{1\ mg/ml,\ 1\ cm}$ ($H_2O$, 20° C.) + 6% |
|---|---|
| 278 (max) | 0.66 |
| 280 | 0.66 |
| 290 | 0.54 |
| 400-1000 | 0 |
| $E_{280}/E_{260}$ | 1.23 |

10. Chemotaxin (granulocyto-monotaxin) according to claim 8, characterized in that it is obtainable from granulocytes and possesses the following additional properties:

(a) biological activities:

chemical attraction of macrophages (monocytes) in vitro;

accumulation or monocytic leukocytes in situ with indirect, cell-induced angiogenesis and inflammation reaction;

effective threshold dose in vitro: <10 nmol/l;

(b) physico-chemical properties:

molecular weight of the native protein (primary structure): approximately 17,000 dalton;

absorption spectrum (UV, visible and near IR-range) as given in FIG. 6;

extinction coefficient according to the following Table VI:

TABLE VI

| Wave length, nm | $E_{1\ mg/ml,\ 1\ cm}$ ($H_2O$, 20° C.) + 6% |
|---|---|
| 249 (min) | 0.36 |
| 260 | 0.43 |
| 278 (max) | 0.60 |
| 280 | 0.59 |
| 290 | 0.34 |
| 400-1000 | 0 |
| $E_{280}/E_{260}$ | 1.37 |

11. Chemotaxin (monocyto-eosinotaxin) according to claim 8, characterized in that it is obtainable from mononuclear leukocytes and possesses the following additional properties:

(a) biological activities:

chemical attraction of eosinophilic leukocytes in vitro;

accumulation of eosinophilic leukocytes in situ;

effective threshold dose in vitro; <5 nmol/l;

(b) physico-chemical properties:

molecular weight of the native protein (primary structure): approximately 5,000 dalton;

no protein quaternary structure in the form of physically bound peptide subunits: each of the native proteins consists of only one peptide unit;

absorption spectrum (UV, visible and near IR-range) as given in FIG. 7;

extinction coefficient according to the following Table VII:

TABLE VII

| Wave length, nm | $E_{1\ mg/ml,\ 1\ cm}$ ($H_2O$, 20° C.) + 6% |
|---|---|
| 252 (min) | 0.33 |
| 260 | 0.39 |
| 277 (max) | 0.53 |
| 280 | 0.53 |
| 290 | 0.39 |
| 400-1000 | 0 |
| $E_{280}/E_{260}$ | 1.36 |

12. A pharmaceutical composition for specifically influencing the immune system and inflammatory processes of mammalians, comprising an effective amount of at least one leukocyte derived chemokinesin or chemotaxin according to claim 1 and a suitable carrier therefor.

13. A pharmaceutical composition for specifically influencing the immune system and inflammatory processes of mammalians, comprising an effective amount of at least one leukocyte derived antichemokinesin or chemotaxin immunoglobulin.

14. A method for specifically influencing the immune system and inflammatory processes of mammalians comprising administering an effective amount of at least one leukocyte derived chemokinesin or chemotaxin according to claim 1.

15. A method for specifically influencing the immune system and inflammatory processes of mammalians comprising administering an effective amount of at least one leukocyte derived anti-chemokinesin or chemotaxin immunoglobulin.

16. A process for isolating and purifying leukocyte derived chemokinesins and chemotaxins according to claim 1, which comprises:

(a) culturing leukocytes in a suitable culture medium;
(b) separating said leukocytes from said medium to yield a culture solution;
(c) adding a sufficient amount of a suitable salt to precipitate a first protein fraction from said culture solution;
(d) separating said first protein portion from said solution;
(e) concentrating said solution to obtain a second protein fraction therefrom;
(f) separately purifying said first and second protein fractions by molecular sieve filtration, anion and cation exchange chromatography, chromatography on hydroxypapatite, zone precipitation chromatography, or recycling molecular sieve filtration to obtain said chemokinesins.

17. The process according to claim 16, wherein a mixed leukocyte population is cultured.

18. The process according to claim 16, wherein a specific leukocyte type is cultured.

19. The process according to claim 15, wherein the leukocytes are cultured in a fully synthetic cell culture medium containing serum albumin as the only protein.

20. The process according to claim 15, wherein leukocyte mitosis is induced during the culturing.

21. The process according to claim 20, wherein a polyvalent mitogen or endotoxin-mitogen is added or an immune reaction is promoted on the cell surface so as to induce the mitosis of the leukocytes.

22. The process according to claim 21, wherein leukocyte mitosis is induced by the addition of a lectin.

23. The process according to claim 22, wherein a lectin from *Canavalia ensiformis* (Concanavalin A=-CON) is used.

24. The process according to claim 19, wherein leukocytes are cultured in a cell culture medium having the composition given in Table VIII.

25. The process according to claim 24, wherein the leukocytes are cultured for approximately 40 hours at about 37° C. and a concentration of about $10^7$ to $10^8$ cells/ml culture solution at a $CO_2$-partial pressure of about 1% while sufficient oxygen is supplied to the culture.

26. The process according to claim 25, wherein ammonium sulfate is used for precipitating the proteins.

27. The process according to claim 26, wherein the ammonium sulfate concentration of the culture solution is stepwise increased and the proteins precipitated after each ammonium sulfate addition are separated, thereby yielding several crude protein fractions having differing solubilities at different ammonium sulfate concentration.

28. The process according to claim 27, wherein the ammonium sulfate concentration of the culture solution is adjusted stepwise to 35%, 45% and 90% saturation.

29. The process according to claim 25, wherein the supernatant after separation of the protein precipitate is concentrated by ultrafiltration or dialysis.

30. The process according to claim 25, wherein at least two of the said purification steps are performed in sequence.

31. The process according to claim 30, wherein at least three of the said purification steps are performed in sequence.

32. A process for producing lymphocytomonoapokinesin which comprises:

(a) culturing a leukocyte cell population including mixed leukocytes or only lymphocytes;
(b) terminating culturing;
(c) separating the cells from the culture medium after termination of culturing to yield a culture solution;
(d) adding ammonium sulfate to the culture solution up to 90% saturation in order to precipitate proteins contained therein;
(e) separating the precipitated proteins from the ammonium sulfate containing supernatant;
(f) redissolving the precipitated proteins;
(g) purifying said proteins by anion exchange chromatography, preparative molecular sieve filtration, cation exchange chromatography, chromatography on hydroxyapatite, zone precipitation chromatography and recycling molecular sieve filtration; and
(h) isolating the lymphocytomonoapokinesin from the eluate of the recycling molecular sieve filtration by adding ammonium sulfate up to about 80–90% saturation and separating the precipitate formed from the supernatant.

33. A process for producing highly purified monocytogranuloapokinesin which comprises:

(a) culturing a leukocyte cell population containing mixed leukocytes or only monocytes;
(b) inducing the mitosis of the cells by CON during culturing;
(c) terminating culturing;
(d) separating the cells from the culture medium after termination of culturing to yield a culture solution;
(e) adding sufficient ammonium sulfate to the culture solution to provide an ammonium sulfate concentration of up to 90% saturation to precipitate proteins contained therein;
(f) separating the precipitated proteins from the ammonium sulfate containing supernatant;
(g) redissolving the precipitated proteins;
(h) purifying said proteins by anion exchange chromatography, preparative molecular sieve filtration, cation exchange chromatography, chromatography on hydroxyapatite, zone precipitation chromatography, and recycling molecular sieve filtration; and
(i) isolating the monocytogranuloapokinesin from the eluate of the recycling molecular sieve filtration by adding ammonium sulfate up to about 80–90% saturation and separating the precipitate formed from the supernatant.

34. A process for producing molecularly homogeneous monocytogranuloproskinesin which comprises:

(a) culturing a leukocyte cell population containing mixed leukocytes or only monocytes;
(b) inducing the mitosis of the cells by CON during culturing;
(c) terminating culturing;
(d) separating the cells from the culture medium after termination of culturing to form a culture solution;
(e) adding ammonium sulfate to the culture solution up to 90% saturation in order to precipitate proteins contained therein;
(f) separating the precipitated proteins from the ammonium sulfate containing supernatant;
(g) redissolving the precipitated proteins;
(h) purifying said proteins by anion exchange chromatography, preparative molecular sieve filtration, cation exchange chromatography, chromatography on hyroxyapatite, zone precipitstion chromatography and recycling molecular sieve filtration; and
(i) isolating the monocytogranuloproskinesin from the eluate of the recycling molecular sieve filtration by adding ammonium sulfate up to about 80–90% saturation and separating the precipitate formed from the supernatant.

35. A process for producing highly purified lymphocytomonoproskinesin which comprises:

(a) culturing a leukocyte cell population containing mixed leukocytes or only lymphocytes;
(b) inducing the mitosis of the cells by CON during culturing;
(c) terminating culturing;
(d) separating the cells from the culture medium after termination of culturing to yield a culture solution;
(e) adding ammonium sulfate to the culture solution up to 90% saturation to precipitate proteins contained therein;
(f) separating the precipitated proteins from the ammonium sulfate containing supernatant;
(g) redissolving said precipitated proteins;
(h) purifying said proteins by anion exchange chromatography, preparative molecular sieve filtration, cation exchange chromatography, chromatography on hydroxyapatite, zone precipitation chromatography and recycling molecular sieve filtration; and
(i) isolating the lympohocytomonoproskinesin from the eluate of the recycling molecuar sieve filtration by adding ammonium sulfate up to about 80–90% saturation and separating the precipitate from the supernatant.

36. A process for producing highly purified monocytogranulotaxin which comprises:

(a) culturing a leukocyte cell population containing mixed leukocytes or only monocytes;
(b) inducing the mitosis of the cells by CON during culturing;
(c) terminating culturing;
(d) separating the cells from the culture medium after terminating culturing to yield a culture solution;
(e) adding ammonium sulfate to the culture solution up to 90% saturation to precipitate proteins concentrated therein;
(f) separating the precipitated proteins from the ammonium sulfate containing supernatant;
(g) redissolving said precipitated proteins;
(h) purifying said proteins by anion exchange chromatography, preparative molecular sieve filtration, cation exchange chromatography, chromatography on hydroxyapatite, zone prcipitation chromatography and recycling molecular sieve filtration; and
(i) isolating the monocytogranulotaxin from the eluate of the recycling molecular sieve filtration by adding ammonium sulfate up to about 80–90% saturation and separating the precipitate formed from the supernatant.

37. A process for preparing highly purified granulocytomonotaxin which comprises:

(a) culturing a leukocyte cell population containing mixed leukocytes or only granulocytes;
(b) inducing the mitosis of the cells by CON during culturing;
(c) terminating culturing;
(d) separating the cells from the culture medium after terminating culturing to yield a culture solution;
(e) adding ammonium sulfate to the culture solution to achieve up to 90% saturation in order to precipitate proteins contained therein;
(f) separating the precipitated proteins from the ammonium sulfate containing supernatant;
(g) redissolving said proteins;
(h) purifying said proteins by anion exchange chromatography, preparative molecular sieve filtration, cation exchange chromatography, chromatography on hydroxyapatite, zone precipitation chromatography and recycling molecular sieve filtration; and
(i) isolating the granulocytomonotaxin in highly purified form in the eluate of the recycling molecular sieve filtration by adding ammonium sulfate up to about 80–90% saturation and separating the precipitate formed from the supernatant.

38. A process for producing monocytoeosinotaxin which comprises:

(a) culturing a leukocyte cell population containing mixed leukocytes or only monocytes;
(b) inducing the mitosis of the cells by CON during culturing;
(c) terminating culturing;
(d) separating the cells from the culture medium after terminating culturing to yield a culture solution;
(e) adding ammonium sulfate to the culture solution to achieve up to a 90% saturation in order to precipitate proteins contained therein;
(f) separating the precipitated proteins from the ammonium sulfate containing supernatant;
(g) redissolving the precipitated proteins;
(h) purifying said proteins by anion exchange chromatography, preparative molecular sieve filtration, cation exchange chromatography, chromatography on hydroxyapatite, zone precipitation chromatography and recycling molecular sieve filtration; and
(i) isolating the monocytoeosinotaxin in highly purified form in the eluate of the recycling molecular sieve filtration by adding ammonium sulfate up to about 80–90% saturation and separating the precipitate formed from the supernatant.

39. The process according to any one of claims 15 and 26 to 38, wherein the soluble portion of a leukocyte or inflamed tissue homogenate is used instead of the culture solution of the leukocytes.

40. Highly purified lymphocytomonoapokinesin.
41. Highly purified monocytogranuloapokinesin.
42. Highly purified monocytogranuloproskinesin.
43. Highly purified lymphocytomonoproskinesin.
44. Highly purified monocytogranulotaxin.
45. Highly purified granulocytomonotaxin.
46. Highly purified monocytoeosinotaxin.

* * * * *